US00RE49625E

(19) United States
(12) Reissued Patent
Sierks et al.

(10) Patent Number: US RE49,625 E
(45) Date of Reissued Patent: Aug. 29, 2023

(54) NANOSCALE PROCESS TO GENERATE REAGENTS SELECTIVE FOR INDIVIDUAL PROTEIN VARIANTS

(71) Applicant: Arizona Board of Regents, a Body Corporate of the State of Arizona, Acting For and on Behalf of Arizona State University, Scottsdale, AZ (US)

(72) Inventors: Michael Sierks, Ft. McDowell, AZ (US); Mark Hayes, Gilbert, AZ (US)

(73) Assignee: ARIZONA BOARD OF REGENTS, A BODY CORPORATE OF THE STATE OF ARIZONA, Scottsdale, AZ (US), ACTING FOR AND ON BEHALF OF ARIZONA STATE UNIVESITY

(21) Appl. No.: 16/845,761

(22) Filed: Apr. 10, 2020

Related U.S. Patent Documents

Reissue of:
(64) Patent No.: 9,938,330
Issued: Apr. 10, 2018
Appl. No.: 14/388,209
Filed: Sep. 25, 2014

U.S. Applications:
(60) Provisional application No. 61/617,476, filed on Mar. 29, 2012.

(51) Int. Cl.
*C07K 14/47* (2006.01)
*B03C 5/00* (2006.01)
(Continued)

(52) U.S. Cl.
CPC ..... *C07K 14/4711* (2013.01); *B03C 5/005* (2013.01); *B03C 5/026* (2013.01);
(Continued)

(58) Field of Classification Search
CPC ... B03C 5/026; G01N 27/447; C07K 14/4711
See application file for complete search history.

(56) References Cited

U.S. PATENT DOCUMENTS 7,014,747 B2 3/2006 Cummings et al.
7,347,923 B2 3/2008 Cummings et al.
(Continued)

FOREIGN PATENT DOCUMENTS

WO 1994010205 A1 5/1994
WO 2004013172 A2 2/2004
(Continued)

OTHER PUBLICATIONS

Nakano. Electrophoresis. Sep. 2011; 32(17): 2314-2322 (Year: 2011).*
(Continued)

*Primary Examiner* — Padmashri Ponnaluri
*Assistant Examiner* — Jean C Witz
(74) *Attorney, Agent, or Firm* — Duane Morris LLP

(57) ABSTRACT

The present invention provides devices and methods to separate and concentrate target protein species at a micro-liter scale and to generate reagents to those variants with exquisite selectivity for specific protein isoforms using only picograms of target material.

19 Claims, 9 Drawing Sheets

Specification includes a Sequence Listing.

(51) Int. Cl.
*B03C 5/02* (2006.01)
*G01N 27/447* (2006.01)
*B01L 3/00* (2006.01)

(52) U.S. Cl.
CPC ..... *G01N 27/447* (2013.01); *B01L 3/5027* (2013.01); *B03C 2201/26* (2013.01)

(56) References Cited

U.S. PATENT DOCUMENTS

| | | | | |
|---|---|---|---|---|
| 7,897,361 | B2 | 3/2011 | Westbrook et al. | |
| 2008/0107601 | A1 | 5/2008 | Lauwereys et al. | |
| 2008/0305498 | A1* | 12/2008 | Milewicz ..... | G01N 33/6803 435/7.21 |
| 2009/0294291 | A1 | 12/2009 | Voldman et al. | |
| 2011/0044986 | A1 | 2/2011 | Biere-Citron et al. | |
| 2011/0108422 | A1 | 5/2011 | Heller et al. | |

FOREIGN PATENT DOCUMENTS

| | | | |
|---|---|---|---|
| WO | 2006040153 | A2 | 4/2006 |
| WO | 2011031720 | A1 | 3/2011 |
| WO | 2012/058334 | A1 | 5/2012 |

OTHER PUBLICATIONS

Horiuchi et al., (2007). "Electroosmosis with step changes in zeta potential in microchannels." AIChE Journal 53: 2521-2533.
Patent Cooperation Treaty, International Searching Authority, Search Report and Written Opinion for PCT/US2013/30563, 10 pages, May 22, 2013.
Nannenga, Brent L., Andleeb Zameer, and Michael R. Sierks. "Anti-oligomeric single chain variable domain antibody differentially affects huntingtin and α-synuclein aggregates." FEBS Letters 582. 4 (2008): 517-522.
Kvam E, Sierks MR, Shoemaker CB, Messer A. "Physico-chemical determinants of soluble intrabody expression in mammalian cell cytoplasm." Protein Eng Des Sel. 2010;23(6):489-498. with supplement; doi:10.1093/protein/gzq022.
Jones et al., Blood cell capture in a sawtooth dielectrophoretic microchannel, Anal Bioanal Chem 401: pp. 2103-2111, available online Aug. 4, 2011.*
Chiti et al., (2006). "Protein misfolding, functional amyloid, and human disease." Annu. Rev. Biochem. 75: 333-366.
Selkoe, (2008). "Soluble oligomers of the amyloid beta-protein impair synaptic plasticity and behavior." Behav. Brain Res. 192: 106-113.
Cobb et al., (2009). "Prion diseases and their biochemical mechanisms." Biochemistry 48: 2574-2585.
Selkoe, (1989). "The deposition of amyloid proteins in the aging mammalian brain: implications for Alzheimer's disease." Ann Me 21: 73-76.
Dahlgren et al., (2002). "Oligomeric and fibrillar species of amyloid-beta peptides differentially affect neuronal viability." J. Biol. Chem. 277: 32046-32053.
Deshpande et al., (2006). "Different conformations of amyloid beta induce neurotoxicity by distinct mechanisms in human cortical neurons." J. Neurosci. 26: 6011-6018.
Lambert et al., (1998). "Diffusible, nonfibrillar ligands derived from Abeta1-42 are potent central nervous system neurotoxins." Proc. Natl. Acad. Sci. USA 95: 6448-6453.
Lesne et al., (2006). "A specific amyloid-beta protein assembly in the brain impairs memory." Nature 440: 352-357.
Selkoe, (2000). "Toward a comprehensive theory for Alzheimer's disease. Hypothesis: Alzheimer's disease is caused by the cerebral accumulation and cytotoxicity of amyloid beta-protein." Ann. NY Acad. Sci. 924: 17-25.
Lue et al., (1999). "Soluble amyloid beta peptide concentration as a predictor of synaptic change in Alzheimer's disease." Am. J. Pathol. 155: 853-862.
McLean et al., (1999). "Soluble pool of Abeta amyloid as a determinant of severity of neurodegeneration in Alzheimer's disease." Ann. Neurol. 46: 860-866.
Walsh et al., (1999). "Amyloid beta-protein fibrillogenesis. Structure and biological activity of protofibrillar intermediates." J. Biol. Chem. 274: 25945-25952.
Harper et al., (1997). "Observation of metastable Aβ amyloid protofibrils by atomic force microscopy." Chemistry & Biology 4: 119-125.
Wang et al., (2002). "Soluble oligomers of beta amyloid (1-42) inhibit long-term potentiation but not long-term depression in rat dentate gyrus." Brain Res. 924: 133-140.
Walsh et al., (2002). "Naturally secreted oligomers of amyloid beta protein potently inhibit hippocampal long-term potentiation in vivo." Nature 416: 535-539.
Chang et al., (2003). "Femtomole immunodetection of synthetic and endogenous amyloid-beta oligomers and its application to Alzheimer's disease drug candidate screening." J. Mol. Neurosci. 20: 305-313.
Gong et al., (2003). "Alzheimer's disease-affected brain: presence of oligomeric A beta ligands (ADDLs) suggests a molecular basis for reversible memory loss." Proc. Natl. Acad. Sci. USA 100: 10417-10422.
Tsai et al., (2004). "Fibrillar amyloid deposition leads to local synaptic abnormalities and breakage of neuronal branches." Nat. Neurosci. 7: 1181-1183.
Koffie et al., (2009). "Oligomeric amyloid beta associates with postsynaptic densities and correlates with excitatory synapse loss near senile plaques." Proc. Natl. Acad. Sci. USA 106: 4012-4017.
Cleary et al., (2005). "Natural oligomers of the amyloid-beta protein specifically disrupt cognitive function." Nat. Neurosci. 8: 79-84.
Townsend et al., (2006). "Effects of Secreted Oligomers of Amyloid {beta}-Protein on Hippocampal Synaptic Plasticity: A Potent Role for Trimers." J. Physiol. 572(Pt 2): 477-492.
Walsh et al., (2005). "The role of cell-derived oligomers of Abeta in Alzheimer's disease and avenues for therapeutic intervention." Biochem. Soc. Trans. 33: 1087-1090.
Lambert et al., (2001). "Vaccination with soluble Abeta oligomers generates toxicity-neutralizing antibodies." J. Neurochem. 79: 595-605.
Kayed et al., (2003). "Common structure of soluble amyloid oligomers implies common mechanism of pathogenesis." Science 300: 486-489.
Lacor et al., (2004). "Synaptic targeting by Alzheimer's-related amyloid beta oligomers." J. Neurosci. 24: 10191-10200.
Klein et al., (2004). "Small assemblies of unmodified amyloid beta-protein are the proximate neurotoxin in Alzheimer's disease." Neurobiol. Aging 25: 569-580.
Cummings et al., (2003). "Dielectrophoresis in Microchips Containing Arrays of Insulating Posts: Theoretical and Experimental Results." Anal. Chem. 75: 4724-4731.
Cummings, (2003). "Streaming Dielectrophoresis for Continuous-Flow Microfluidic Devices." IEEE Engineering in Medicine and Biology Magazine, Nov./Dec.: 75-84.
Lapizco-Encinas et al., (2004). "Insulator-based dielectrophoresis for the selective concentration and separation of live bacteria in water." Electrophoresis 25: 1695-1704.
Lapizco-Encinas et al., (2004). "Dielectrophoretic Concentration and Separation of Live and Dead Bacteria in an Array of Insulators." Anal. Chem. 76: 1571-1579.
Barrett et al., (2005). "Dielectrophoretic manipulation of particles and cells using insulating ridges in faceted prism microchannels." Analytical Chemistry 77: 6798-6804.
Lapizco-Encinas et al., (2005). "An insulator-based (electrodeless) dielectrophoretic concentrator for microbes in water." Journal of Microbiological Methods 62: 317-326.
Simmons et al., (2006). "The development of polymeric devices as dielectrophoretic separators and concentrators." MRS Bulletin 31: 120-124.
Davalos et al., (2008). "Performance impact of dynamic surface coatings on polymeric insulator-based dielectrophoretic particle separators." Analytical and Bioanalytical Chemistry 390: 847-855.

(56) References Cited

OTHER PUBLICATIONS

Pysher et al., (2007). "Electrophoretic and dielectrophoretic field gradient technique for separating bioparticles." Analytical Chemistry 79: 4552-4557.
Chen et al., (2009). "Insulator-based Dielectrophoretic Separations of Small Particles in Sawtooth Channel." Electrophoresis 30: 1441-1448.
Staton et al., (2010). "Characterization of particle capture in a sawtooth patterned insulating electrokinetic microfluidic device." Electrophoresis 31: 3634-3641.
Weiss et al., (2011). "Dielectrophoretic mobility determination in DC insulator-based dielectrophoresis." Electrophoresis 32: 2292-2297.
Washizu et al., (1996). "Generalized multipolar dielectrophoretic force and electrorotational torque calculation." Journal of Electrostatics 38: 199-211.
Barkhordarian et al., (2006). "Isolating recombinant antibodies against specific protein morphologies using atomic force microscopy and phage display technologies." Protein Eng. Des. Sel. 19: 497-502.
Shlyakhtenko et al., (2007). "Single-molecule selection and recovery of structure-specific antibodies using atomic force microscopy." Nanomedicine 3: 192-197.
Wang et al., (2009). "Characterizing Antibody Specificity to Different Protein Morphologies by AFM." Langmuir 25: 912-918.
Emadi et al., (2004). "Inhibiting Aggregation of alpha-Synuclein with Human Single Chain Antibody Fragments." Biochemistry 43: 2871-2878.
Zhou et al., (2004). "A human single-chain Fv intrabody blocks aberrant cellular effects of overexpressed alpha-synuclein." Mol. Ther. 10: 1023-1031.
Liu et al., (2004). "Single chain variable fragments against beta-amyloid (Abeta) can inhibit Abeta aggregation and prevent abeta-induced neurotoxicity." Biochemistry 43: 6959-6967.
Zameer et al., (2006). "Single Chain Fv Antibodies against the 25-35 Abeta Fragment Inhibit Aggregation and Toxicity of Abeta42." Biochemistry 45: 11532-11539.
Marcus et al., (2008). "Characterization of an antibody scFv that recognizes fibrillar insulin and beta-amyloid using atomic force microscopy." Nanomedicine 4: 1-7.
Emadi et al., (2007). "Isolation of a human single chain antibody fragment against oligomeric alpha-synuclein that inhibits aggregation and prevents alpha-synuclein-induced toxicity." J. Mol. Biol. 368: 1132-1144.
Emadi et al., (2009). "Detecting morphologically distinct oligomeric forms of alpha-synuclein." J. Biol. Chem. 284: 11048-11058.
Zameer et al., (2008). "Anti-oligomeric Abeta single-chain variable domain antibody blocks Abeta-induced toxicity against human neuroblastoma cells." J. Mol. Biol. 384: 917-928.
Kasturirangan et al., (2010). "Nanobody specific for oligomeric beta-amyloid stabilizes non-toxic form." Neurobiology of Aging 33(7): 1320-1328.
Roychaudhuri et al., (2009). "Amyloid beta-Protein Assembly and Alzheimer Disease." Journal of Biological Chemistry 284: 4749-4753.
Picou et al., (2010). "Analysis of monomeric A beta (1-40) peptide by capillary electrophoresis." Analyst 135: 1631-1635.
Picou et al., (2011). "Analysis of A-beta (1-40) and A-beta (1-42) Monomer and Fibrils by Capillary Electrophoresis." Journal of Chromatography B 879: 627-632.
Lapizco-Encinas et al., (2008). "Protein manipulation with insulator-based dielectrophoresis and direct current electric fields." Journal of Chromatography A 1206: 45-51.
Clarke et al., (2005). "Trapping of proteins under physiological conditions in a nanopipette." Angewandte Chemie-International Edition 44: 3747-3750.
Holzel et al., (2005). "Trapping single molecules by dielectrophoresis." Physical Review Letters 95: 128102.
Wang et al., (2008). "Covalent modified hydrophilic polymer brushes onto poly(dimethylsiloxane) microchannel surface for electrophoresis separation of amino acids." Journal of Chromatography A 1192: 173-179.
Lucy et al., (2008). "Non-covalent capillary coatings for protein separations in capillary electrophoresis." Journal of Chromatography A 1184: 81-105.
Mansfield et al., (2007). "Preparation and characterization of cross-linked phospholipid bilayer capillary coatings for protein separations." Analytical Chemistry 79: 3135-3141.
Mohamadi et al., (2007). "Dynamic coating using methylcellulose and polysorbate 20 for nondenaturing electrophoresis of proteins on plastic microchips." Electrophoresis 28: 830-836.
Liu et al., (2007). "Poly(dimethylsiloxane) microchips with two sharpened stretching tips and its application to protein separation using dynamic coating." Chinese Journal of Chemistry 25: 190-195.
MacDonald et al., (2006). "Highly efficient protein separations in capillary electrophoresis using a supported bilayer/diblock copolymer coating." Journal of Chromatography A 1130: 265-271.
Zhang et al., (2006). "Poly(N,N-dimethylacrylamide)-grafted polyacrylamide: A self-coating copolymer for sieving separation of native proteins by CE." Electrophoresis 27: 3086-3092.
Huang et al., (2005). "Coating of poly(dimethylsiloxane) with n-dodecyl-beta-D-maltoside to minimize nonspecific protein adsorption." Lab on a Chip 5: 1005-1007.
Gu et al., (2005). "Preparation and evaluation of poly (polyethylene glycol methyl ether acrylate-co-polyethylene glycol diacrylate) monolith for protein analysis." Journal of Chromatography A 1079: 382-391.
Hellmich et al., (2005). "Poly(oxyethylene) based surface coatings for poly(dimethylsiloxane) microchannels." Langmuir 21: 7551-7557.
Ros et al., (2006). "Bioanalysis in structured microfluidic systems." Electrophoresis 27: 2651-2658.
Lee et al., (2005). "An aqueous-based surface modification of poly(dimethylsiloxane) with poly(ethylene glycol) to prevent biofouling." Langmuir 21: 11957-11962.
Wong et al., (2009). "Surface molecular property modifications for poly(dimethylsiloxane) (PDMS) based microfluidic devices." Microfluidics and Nanofluidics 7: 291-306.
Zhou et al., (2009). "Convenient Method for Modifying Poly(dimethylsiloxane) with Poly(ethylene glycol) in Microfluidics." Analytical Chemistry 81: 6627-6632.
Chen et al., (2008). "Biocompatible polymer materials: Role of protein-surface interactions." Progress in Polymer Science 33: 1059-1087.
Sugiura et al., (2008). "Surface modification of polydimethylsiloxane with photo-grafted poly(ethylene glycol) for micropatterned protein adsorption and cell adhesion." Colloids and Surfaces B-Biointerfaces 63: 301-305.
Jung et al., (2008). "A cell-repellent sulfonated PEG comb-like polymer for highly resolved cell micropatterns." Journal of Biomaterials Science-Polymer Edition 19: 161-173.
Hayes, (1999). "Extension of external voltage control of electroosmosis to high-pH buffers." Analytical Chemistry 71: 3793-3798.
Towns et al., (1990). "Polyethyleneimine-bonded phases in the separation of proteins by capillary electrophoresis." Journal of Chromatography 516: 69-78.
Rosario et al., (2002). "Photon-Modulated Wettability Changes on Spiropyran-Coated Surfaces." Langmuir 18: 8062-8069.
Rosario et al., (2003). "Solvatochromic study of the microenvironment of surface-bound spiropyrans." Langmuir 19: 8801-8806.
Bunker et al., (2003). "Direct Observation of Photo Switching in Tethered Spiropyrans Using the Interfacial Force Microscope." Nano Lett 3: 1723-1727.
Rosario et al., (2004). "Lotus Effect Amplifies Light-Induced Contact Angle Switching." Journal of Physical Chemistry A 108: 12640-12642.
Hayes et al., (1999). "Preservation of NADH voltammetry for enzyme-modified electrodes based on dehydrogenase." Analytical Chemistry 71: 1720-1727.
Liu et al., (2004). "Residues 17-20 and 30-35 of beta-amyloid play critical roles in aggregation." J. Neurosci. Res. 75: 162-171.

(56) References Cited

OTHER PUBLICATIONS

Liu et al., (2004). "Proteolytic antibody light chains alter beta-amyloid aggregation and prevent cytotoxicity." Biochemistry 43: 9999-10007.
Marcus et al., (2006). "Isolation of an scFv targeting BRG1 using phage display with characterization by AFM." Biochem. Biophys. Res. Commun. 342: 1123-1129.
Unger et al., (2000). "Monolithic microfabricated valves and pumps by multilayer soft lithography." Science 288: 113-116.
Shankar et al., (2008). "Amyloid-beta protein dimers isolated directly from Alzheimer's brains impair synaptic plasticity and memory." Nat. Med. 14: 837-842.
Walsh et al., (2000). "The oligomerization of amyloid beta-protein begins intracellularly in cells derived from human brain." Biochemistry 39: 10831-10839.
Kasturirangan et al., (2010). "Engineered Proteolytic Nanobodies Reduce A beta Burden and Ameliorate A beta-Induced Cytotoxicity." Biochem. 49(21): 4501-4508.
Staton et al., (2012). "Manipulation and capture of AB amyloid fibrils and monomers by DC insulator gradient dielectophoresis (DC-iGDEP)." Analyst 137: 3227-3229.
Jones et al., (2011). "Blood cell capture in a sawtooth dielectrophoretic microchannel." Anal. Bioanal. Chem. 401(7): 2103-2111.
Srivastava et al., (2011). "DC insulator dielectrophoretic applications in microdevice technology: a review." Anal. Bioanal. Chem. 399(1): 301-321.
STATON, (2013). "New methods for biological and environmental protein fingerprinting: from traditional techniques to new technology." PhD Dissertation, Arizona State University. repository.asu.edu/attachments/56754/content/Staton_asu_0010E_10534.pdf.
Kasturirangan et al., (2013). "Isolation and Characterization of Antibody Fragments Selective for Specific Protein Morphologies from Nanogram Antigen Samples." Biotechnology Progress 29(2): 463-471.

* cited by examiner

CDR regions

AMINO ACID

C6T SYAMS (SEQ ID NO: 16)

C6T AISGSGGSTYYADSVKG(SEQ ID NO: 17)

C6T SYGSVKISCFDY(SEQ ID NO: 18)

C6T KSSQSVLYNSNNKNYLA(SEQ ID NO: 19)

C6T WASTRES(SEQ ID NO: 20)

C6T QQFYSTPPT(SEQ ID NO: 21)

DNA

Agctatgccatgagc (SEQ ID NO: 22)

Gctattagtggtagtggtggtagcacatactacgcagactccgtgaagggc(SEQ ID NO: 23)

Agctatggttcagttaaaataagctgctttgactac(SEQ ID NO: 24)

Aagtccagccagagtgttctttacaactccaacaataagaactacttagct(SEQ ID NO: 25)

Tgggcatcaacccgggaatcc(SEQ ID NO: 26)

cagcaattttatagtactcctccgact(SEQ ID NO: 27)

>10H (SEQ ID NO:12)

ccatggccgaggtgcagctgttggagtctgggggaggcttggtacagcctgggggtccctgagactctcctgtg
cagcctctggattcacctttagcagctatgccatgagctgggtccgccaggctccagggaaggggctggagtggg
tctcaaatattagtagtgcagggaaggggctggagtgggtctcaagtattgatgattctggtgcttctacatatt
acgcagactccgtgaagggccggttcaccatctccagagacaattccaagaacacgctgtatctgcaaatgaaca
gcctgagagccgaggacacggccgtatattactgtgcgaaagattctgcttcttttgactactggggccagggaa
cctggtcaccgtctcgagcggtggaggcggttcaggcggaggtggcagcggcggtggcgggtcgacggacatcc
agatgacccagtctccatcctccctgtctgcatctgtaggagacagagtcaccatcacttgccgggcaagtcaga
gcattagcagctatttaaattggtatcagcagaaaccagggaaagcccctaagctcctgatctatactgcatcca
gtttgcaaagtggggtcccatcaaggttcagtggcagtggatctgggacagatttcactctcaccatcagcagtc
tgcaacctgaagattttgcaacttactactgtcaacagtctgctgctagtccttctacgttcggccaagggacca
aggtggaaatcaaacgggcggccgcacatcaccatcaccatcacggggccgcagaacaaaaactcntctcagaag
nggatcnnaangggnccg

>D5Q (SEQ ID NO:11)

ccatggccgaggtgcagctgttggagtctgggggaggcttggtacagcctgggggtccctgagactctcctgtg
cagcctctggattcacctttagcagctatgccatgagctgggtccgccaggctccagggaaggggctggagtggg
tctcatcgattggtcagaagggtggtggtacacagtacgcagactccgtgaagggccggttcaccatctccagag
acaattccaagaacacgctgtatctgcaaatgaacagcctgagagccgaggacacggccgtatattactgtgcga
aacattttgagaattttgactactggggccagggaaccctggtcaccgtctcgagcggtggaggcggttcaggcg
gaggtggcagcggcggtggcgggtcgacggacatccagatgacccagtctccatcctccctgtctgcatctgtag
gagacagagtcaccatcacttgccgggcaagtcagagcattagcagctatttaaattggtatcagcagaaaccag
ggaaagcccctaagctcctgatctatgctgcatcccatttgcaaagtggggtcccatcaaggttcagtggcagtg
gatctgggacagatttcactctcaccatcagcagtctgcaacctgaagattttgcaacttactactgtcaacaga
cgcgtaggccgccttctacgttcggccaagggaccaaggtggaaatcaaacgggcggccgcacatcatcatcacc
atcacggggccgcagaacaaaaactcatctcagaagagaatcactagtgcggccgcctgcaggtcgaccata

FIG. 2

>6E (SEQ ID NO:13)

ttgttattactcgcggcccagccggccatggccgaggtgcagctgttggagtctgggggaggcttggtacagcct
gggggtccctgagactctcctgtgcagcctctggattcacctttagcagctatgccatgagctgggtccgccag
gctccagggaaggggctggagtgggtctcatatattgctagtggtggtgatactacaaattacgcagactccgtg
aagggccggttcaccatctccagagacaattccaagaacacgctgtatctgcaaatgaacagcctgagagccgag
gacacggccgtatattactgtgcgaaaggtgcttctgcttttgactactggggccagggaaccctggtcaccgtc
tcgagcggtggaggcggttcaggcggaggtggcagcggcggtggcgggtcgacggacatccagatgacccagtct
ccatcctccctgtctgcatctgtaggagacagagtcaccatcacttgccgggcaagtcagagcattagcagctat
ttaaattggtatcagcagaaaccagggaaagcccctaagctcctgatctatgctgcatcctatttgcaaagtggg
gtcccatcaaggttcagtggcagtggatctgggacagatttcactctcaccatcagcagtctgcaacctgaagat
tttgcaacttactactgtcaacagagttctaatgatccttatacgttcggccaagggaccaaggtggaaatcaaa
cgggcggccgcacatcatcatcaccatcacgggngccnnanaacaaaaactcatctcaaannnnntctgaatggg
ggccncatanactgttgaaagttgtttnnaaacctcntacanaaaantcnnttt

>A4 (SEQ ID NO:8)

ttgttattactcgcggcccagccggccatggccgaggtgcagctgttggagtctgggggaggcttggtacagcct
gggggtccctgagactctcctgtgcagcctctggattcacctttagcagctatcccatgagctgggtccgccag
gctccagggaaggggctggagtgggtctcagcgattcagcatactggtgcgccgacaacttacgcagactccgtg
aagggccggttcaccatctccagagacaattccaagaacacgctgtatctgcaaatgaacagcctgagagccgag
gacacggccgtatattactgtgcgaaagcgtttccgccgtttgactactggggccagggaaccctggtcaccgtc
tcgagcggtggaggcggttcaggcggaggtggcagcggcggtggcgggtcgacggacatccagatgacccagtct
ccatcctccctgtctgcatctgtaggagacagagtcaccatcacttgccgggcaagtcagagcattagcagctat
ttaaattggtatcagcagaaaccagggaaagcccctaagctcctgatctattctgcatcctctttgcaaagtggg
gtcccatcaaggttcagtggcagtggatctgggacagatttcactctcaccatcagcagtctgcaacctgaagat
tttgcaacttactactgtcaacagcgggagactgggcctnnnngttcggncaanggancaangtggaaatcaaac
gggcggccgcacatcatcatcaccatcacggggccgcanaacaaaaactcatctcanaanaggatctgaatgggg
ccgcatanactgttgaaanttgtttancaaacnncatacnnnaaattcattt

>E1 (SEQ ID NO:9)

ttgttattactcgcggcccagccggcctggccgaggtgcagctgttggagtctgggggaggcttggtacagcctg
gggggtccctgagactctcctgtgcagcctctggattcacctttagcagctatgccatgagctgggtccgccagg
ctccagggaaggggctggagtgggtctcatctattcagcctgagggtaggcggacagcgtacgtagactccgtga
agggccggttcaccatctccagagacaattccaagaacacgctgtatctacaaatgaacagcctgagagccgagg
acacggccgtatattactgtgcgaaaccgccggagaggtttgactactggggccagggaaccctggtcaccgtct
cgagcggtggaggcggttcaggcggaggtggcagcggcggtggcgggtcgacggacatccagatgacccagtctc
catcctccctgtctgcatctgtaggagacagagtcaccatcacttgccgggcaagtcagagcattagcagctatt
taaattggtatcagcagaaaccagggaaagcccctaagctcctgatctatgctgcatccagtttgcaaagtgggg
tcccatcaaggttcagtggcagtggatctgggacagatttcactctcaccatcagcagtctgcaacctgaagatt
ttgcaacttactactgtcaacagagttacagtacccctaatacgttcggccaagggaccaaggtggaaatcaaac
gggcggccgcacatcatcatcaccatcacggggccgcagaacaaaaactcatctcanaanaggatctgaatgggg
ccgcatagactgttgaaagttgtttancaaacctcatacagaaaattcattt

FIG. 2
CONTINUED

>D10L2 (SEQ ID NO:14)

atggccgaggtgcagctggtggagtctggggggaggcgtggtccagcctgggaggtccctgagactctcctgtgca
gcctctggattcaccttcagtagctatggcatgcactgggtccgccaggccccaggcaaggggctggagtgggtg
gcagttatatcatatgatggaagtaataaatactatgcagactccgtgaagggccgattcaccatctccagagac
aattccaagaacacgctgtatctgcaagtgaacagcctgagagctgaggacacggccgtgtattactgtgcaaga
attaatgcgaagtggggccaaggtaccctggtcaccgtctcgagtggtggaggcggttcaggcggaggtggctct
ggcggtagtgcacttgacatccagatgacccagtctccatcctccctgtctgcatctgtaggagacagagtcacc
atcacttgccgggcaagtcagagcattagcagctatttaaattggtatcagcagaaaccagggaaagcccctaag
ctcctgatctatgctgcatccagtttgcaaagtggggtcccatcaaggttcagtggcagtggatctgggacagat
ttcactctcaccatcagcagtctgcaacctggagattttgcaacttactactgtcaacagagttacagtaccccg
acgttcgggcaagggaccaaggtggaaatcaaacgtgcggccgcacatcatcatcaccatcacggggccgcagaa
caaaaactcatctcagaagaggatct

>C6 (SEQ ID NO:10)

ccatggcccaggtacagctgcaggagtcgggggaggcttggtacagcctgggggtccctgagactctcctgtgc
agcctctggattcacctttagcagctatgccatgagctgggtccgccaggctccagggaagggggctggagtgggt
ctcagctattagtggtagtggtggtagcacatactacgcagactccgtgaagggccgattcaccatctccagaga
caattccaagaacacgctgtatctgcaaatgaacagcctgagagctgaggacacggctgtgtattactgtgcgaa
gagctatggttcagttaaaataagctgctttgactactggggccagagcaccctggtcaccgtctcctcaggtgg
aggcggttcaggcggaggtggctctggcggtggcggatcggaaattgtgctgacgcagtctccagactccctggc
tgtgtctctgggcgagagggccaccatcaactgcaagtccagccagagtgttctttacaactccaacaataagaa
ctacttagcttggtaccagcagaaaccaggacagtctcctgagttgctcatttactgggcatcaacccgggaatc
cggggtccctgaccgattcagtggcagcgggtctgggacagaattcactcttaccatcagcagcctgcaggctga
ggatgtggcagtttattactgtcagcaattttatagtactcctccgacttttggccaggggaccaagctggagat
caaacgtgcggccgcacatcatcatcaccatcacggggccgcagaacaaaaactcatctcagaagaggatc

Protein

>10H (SEQ ID NO:5)

MAEVQLLESGGGLVQPGGSLRLSCAASGFTFSSYAMSWVRQAPGKGLEWVSNISSAGKGLEWVSSIDDSGASTYY
ADSVKGRFTISRDNSKNTLYLQMNSLRAEDTAVYYCAKDSASFDYWGQGTLVTVSSGGGGSGGGGSGGGGSTDIQ
MTQSPSSLSASVGDRVTITCRASQSISSYLNWYQQKPGKAPKLLIYTASSLQSGVPSRFSGSGSGTDFTLTISSL
QPEDFATYYCQQSAASPSTFGQGTKVEIKRAAAHHHHHHGAAEQKLISEEDLNGAA*

>6E (SEQ ID NO:6)

MAEVQLLESGGGLVQPGGSLRLSCAASGFTFSSYAMSWVRQAPGKGLEWVSYIASGGDTTNYADSVKGRFTISRD
NSKNTLYLQMNSLRAEDTAVYYCAKGASAFDYWGQGTLVTVSSGGGGSGGGGSGGGGSTDIQMTQSPSSLSASVG
DRVTITCRASQSISSYLNWYQQKPGKAPKLLIYAASYLQSGVPSRFSGSGSGTDFTLTISSLQPEDFATYYCQQS
SNDPYTFGQGTKVEIKRAAAHHHHHHGAAEQKLISEEDLNGAA*

FIG. 2
CONTINUED

>D5Q (SEQ ID NO:4)
MAEVQLLESGGGLVQPGGSLRLSCAASGFTFSSYAMSWVRQAPGKGLEWVSSIGQKGGGTQYADSVKGRFTISRD
NSKNTLYLQMNSLRAEDTAVYYCAKHFENPDYWGQGTLVTVSSGGGGSGGGGSGGGGSTDIQMTQSPSSLSASVG
DRVTITCRASQSISSYLNWYQQKPGKAPKLLIYAASHLQSGVPSRFSGSGSGTDFTLTISSLQPEDFATYYCQQT
RRPPSTFGQGTKVEIKRAAAHHHHHHGAAEQKLISEEDLNGAA*

>A4 (SEQ ID NO:2)
MAEVQLLESGGGLVQPGGSLRLSCAASGFTFSSYPMSWVRQAPGKGLEWVSAIQHTGAPTTYADSVKGRFTISRD
NSKNTLYLQMNSLRAEDTAVYYCAKAFPPPFDYWGQGTLVTVSSGGGGSGGGGSGGGGSTDIQMTQSPSSLSASVG
DRVTITCRASQSISSYLNWYQQKPGKAPKLLIYSASSLQSGVPSRFSGSGSGTDFTLTISSLQPEDFATYYCQQR
ETGPKAFGQGTKVEIKRAAAHHHHHHGAAEQKLISEEDLNGAA*

>E1 (SEQ ID NO:3)
MAEVQLLESGGGLVQPGGSLRLSCAASGFTFSSYAMSWVRQAPGKGLEWVSSIQPEGRRTAYVDSVKGRFTISRD
NSKNTLYLQMNSLRAEDTAVYYCAKPPERFDYWGQGTLVTVSSGGGGSGGGGSGGGGSTDIQMTQSPSSLSASVG
DRVTITCRASQSISSYLNWYQQKPGKAPKLLIYAASSLQSGVPSRFSGSGSGTDFTLTISSLQPEDFATYYCQQS
YSTPNTFGQGTKVEIKRAAAHHHHHHGAAEQKLISEEDLNGAA*

>D10L2 (SEQ ID NO:7)
MAEVQLVESGGGVVQPGRSLRLSCAASGFTFSSYGMHWVRQAPGKGLEWVAVISYDGSNKYYADSVKGRFTISRD
NSKNTLYLQVNSLRAEDTAVYYCARINAKWGQGTLVTVSSGGGGSGGGGSGGSALDIQMTQSPSSLSASVGDRVT
ITCRASQSISSYLNWYQQKPGKAPKLLIYAASSLQSGVPSRFSGSGSGTDFTLTISSLQPGDFATYYCQQSYSTP
TFGQGTKVEIKRAAAHHHHHHGAAEQKLISEEDLNGAA*

>C6T (SEQ ID NO:15)
MAQVQLQESGGGLVQPGGSLRLSCAASGFTFSSYAMSWVRQAPGKGLEWVSAISGSGGSTYYADSVKGRFTISRD
NSKNTLYLQMNSLRAEDTAVYYCAKSYGSVKISCFDYWGQSTLVTVSSGGGGSGGGGSGGGGSEIVLTQSPDSLA
VSLGERATINCKSSQSVLYNSNNKNYLAWYQQKPGQSPELLIYWASTRESGVPDRFSGSGSGTEFTLTISSLQAE
DVAVYYCQQFYSTPPTFGQGTKLEIKRAAAHHHHHHGAAEQKLISEEDLNGAA*

FIG. 2
CONTINUED

NANOSCALE PROCESS TO GENERATE REAGENTS SELECTIVE FOR INDIVIDUAL PROTEIN VARIANTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[FEDERAL GRANT] *GOVERNMENT* SUPPORT *CLAUSE*

This invention was made with [Government] *government* support under [Grants No. 2ROIEB004761-06 and R21IEB010191-01A1,] *R01 EB004761 and R21 EB010191* awarded by the National Institutes of Health. The government has certain rights in the invention.

RELATED APPLICATION

*More than one reissue application has been filed for the reissue of U.S. Pat. No. 9,938,330. The reissue applications are U.S. patent application Ser. No. 16/845,761, filed on Apr. 10, 2020, and U.S. patent application Ser. No. 18/134,886, filed Apr. 14, 2023, which is a reissue division of U.S. patent application Ser. No. 16/845,761, all of which are reissues of U.S. Pat. No. 9,938,330.*

This application *is an application for reissue of U.S. Pat. No. 9,938,330, which issued from U.S. application Ser. No. 14,388,209, filed Mar. 12, 2013, which is a 371 of international application PCT/US2013/030563, filed Mar. 12, 2013, and* claims priority to U.S. Provisional Patent Application No. 61/617,476, filed Mar. 29, 2012, [the entirety of which is] *which are* incorporated herein by reference *in their entirety*.

SEQUENCE LISTING

The instant application contains a Sequence Listing which has been submitted in ASCII format via EFS-Web and is hereby incorporated by reference in its entirety. Said ASCII copy, created on [Feb. 21, 2013] *Apr. 23, 2020,* is named [17555.007WO1_SL.txt] *G811802307_SL25.txt* and is [34, 904] *45,584* bytes in size.

BACKGROUND OF THE INVENTION

Protein variants including alternatively processed and misfolded proteins have been associated with many different human diseases. For example, misfolded protein aggregates play a critical role in many devastating human diseases including Alzheimer's (AD) and Parkinson's diseases, diabetes and cancer. However, assessing the variant's role in the onset and progression of different diseases is hampered by a lack of reagents that can distinguish between protein isoforms in vivo. Development of such reagents has been hindered by two main factors: protein variants often occur at only trace levels in vivo and the variants may differ only subtly from the parent form, making them difficult to separate and purify. Novel separation technologies that can tease apart subtle protein variants along with novel molecular recognition protocols are needed to create reagents with sufficient specificity to distinguish between these protein variants. Therefore, there is a continuing need for technologies capable of generating highly selective reagents to specific protein isoforms isolated from mammalian tissue.

SUMMARY OF THE INVENTION

The present invention provides a DC-iGDEP device for separating target protein species in a biological sample based on a variety of chemical and physical parameters comprising an open sawtooth microfluidic channel having an inlet port and an outlet port, and gates between each tooth of the channel, wherein spacing of the gates starts at 50 microns and decreases over two centimeters to 1 micron, and wherein the teeth insulate adjoining gates. As used herein the gap distance of a gate is the distance between teeth across from each other on opposite sides of the device.

The present invention provides a method of separating from a biological sample a target species based on various chemical and physical parameters including charge, size, permittivity, deformation, shape and other factors comprising (a) providing the device for separating target protein species in a biological sample based on a variety of chemical and physical parameters comprising an open sawtooth microfluidic channel having an inlet port and an outlet port, and gates between each tooth of the channel, wherein spacing of the gates starts at 50 microns and decreases over two centimeters to 1 micron, and wherein the teeth insulate adjoining gates, (b) loading a loading volume of the sample into the inlet port, (c) applying a field to the device to separate particles or molecules in the sample, and (d) recovering the target species.

In certain embodiments, the target species is an Aβ aggregate. In certain embodiments, the recovered Aβ aggregates with an antibody to confirm the size of the Aβ aggregate. In certain embodiments, the antibody is specific for oligomeric Aβ aggregates. As used herein, the term "oligomer" refers to a dimer, trimer, or tetramer or larger aggregate. In certain embodiments, the antibody is a nanobody. As used herein, the term "antibody" includes scFv (also called a "nanobody"), humanized, fully human or chimeric antibodies, single-chain antibodies, diabodies, and antigen-binding fragments of antibodies (e.g., Fab fragments). In certain embodiments, the nanobody is a C6, A4, E1, D5, 10H, 6E, D10 or BSEC1 nanobody.

In certain embodiments, the biological sample has a volume of less than 100 microliters. In certain embodiments, has a volume of about 50 microliters. In certain embodiments, the biological sample is brain tissue, serum, cerebrospinal fluid (CSF), urine or saliva. In certain embodiments, the force is applied for a period of time that is less than 20 minutes, such as between 5-15 minutes. In certain embodiments, target Aβ aggregate is concentrated by several orders of magnitude. In certain embodiments, the target Aβ aggregate is concentrated by $10^6$ as compared to the loading volume. In certain embodiments, the protein is p53, islet amyloid polypeptide, beta-amyloid, tau), alpha-synuclein, huntingtin, or superoxide dismutase.

BRIEF DESCRIPTION OF THE FIGURES

FIG. 2 provides nucleic acid and amino acid sequences for several nanobodies. Underlining indicates CDR regions (or nucleic acids that encode CDR regions).

DETAILED DESCRIPTION OF THE INVENTION

Figure 1:
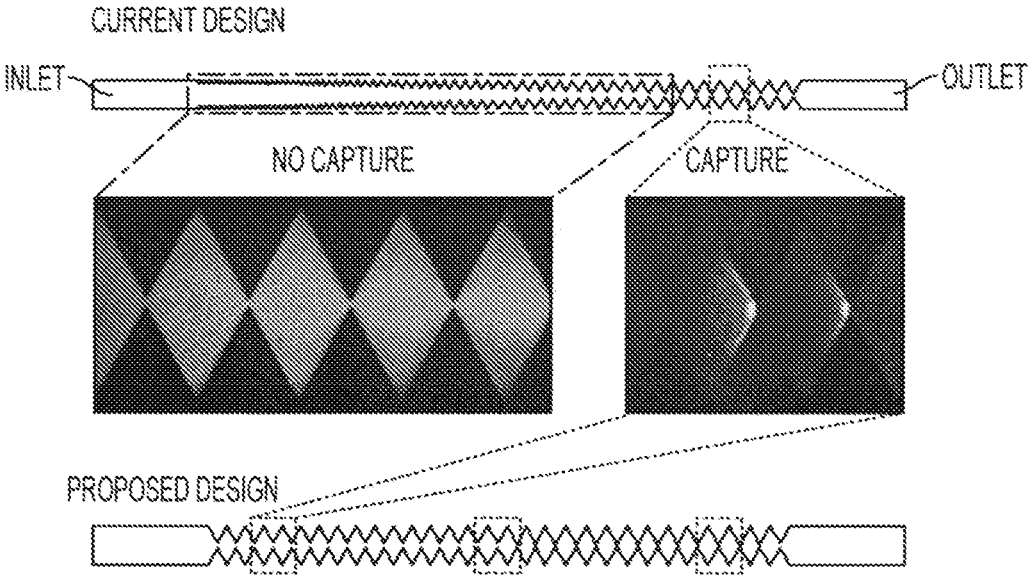
FIG. 1. Schematic showing current DC-iGDEP design (top) used to capture Aβ fibrils (middle, right) but not monomers (middle, left). The proposed modified device (bottom) will 1) increase maximum DEP force ~700 times to capture monomeric Aβ, 2) refine the difference in local DEP force between adjoining "gates," and 3) enable separation and concentration of various Aβ aggregates (dimers, trimers, . . . up to fibrils) in separate chambers.

The inventors have developed methods to separate and concentrate protein variants at a microliter scale and to generate reagents to those variants with exquisite selectivity for specific protein isoforms using only picograms of target material. This capability is broadly applicable to protein variants associated with many human diseases. In certain embodiments, this method is used to generate reagents against isoforms of the protein amyloid-beta (Aβ) that have been implicated in Alzheimer's disease (AD). Misfolding and assembly of Aβ into an array of different aggregate species has been linked to the onset and progression of AD. A variety of different length and aggregate forms of Aβ have been identified in human brain tissue. Unique Aβ forms present in AD brain tissue are separated and isolated using a novel electric field-based separation process. Antibody-based reagents are utilized that can selectively bind the different Aβ species and identify which reagents can best distinguish healthy and AD brain tissue.

The present work benefits from the current availability of well characterized post-mortem human AD and healthy brain tissue. The present work utilizes novel electric field-based capabilities, which can quickly isolate and concentrate different protein isoforms using only minimal amounts of material. This enables the collection in separate nanoliter volumes several distinct Aβ isoforms isolated from human AD tissue. Novel protocols have been developed that allow the isolation of single chain variable domain antibody fragments (scFvs, also called "nanobodies") against specific protein morphologies by utilizing Atomic Force Microscopy (AFM) in conjunction with surface display antibody libraries. These protocols enable the isolation of nanobodies to specific aggregate morphologies using only picograms of material without the need for any protein modification. Panning techniques are used to generate nanobodies against the isolated Aβ isoforms from AD tissue. Protocols have been developed to characterize nanobody binding specificity to different target morphologies without the need to purify or modify the target antigen and again requiring only microliters of protein target solution. Techniques have been developed both to isolate subtle protein variants involved in human disease, in this case Aβ isoforms isolated from AD brain tissue, and also to generate and characterize nanobody reagents to the key isoforms that distinguish AD from healthy brain tissue.

Understanding the molecular basis of disease progression is often a very challenging and complex problem because the specific biochemical species involved may be extremely difficult to identify. Individual biomolecules may be unstable and differ from each other in only very subtle ways, therefore identification and isolation of different forms is a technologically demanding problem. One critically important and challenging class of closely related protein variants are different folded conformations of the same protein. Misfolded and aggregated protein variants are often indistinguishable by many analytical strategies. Over 30 human health diseases have already been connected to misfolding or misprocessing of proteins including cancer (p53), diabetes (islet amyloid polypeptide), Alzheimer's (beta-amyloid and tau), Parkinson's (alpha-synuclein), and Huntington's diseases (huntingtin), Amyotrophic lateral sclerosis (superoxide dismutase) and prion based diseases. In many of these diseases, specific misfolded protein variants such as small soluble oligomeric forms of the amyloid-beta (Aβ) protein or a misfolded form of the prion protein have been associated with cell dysfunction and disease progression. While the role of protein expression in disease can be very effectively studied using proteomic and genomic analyses or inhibitory RNA techniques, these methods are generally not capable of distinguishing between misfolded or alternatively processed protein variants. The different protein variants are often metastable and contain only subtle differences. Robust tools that can selectively identify and manipulate aberrant protein forms would be extremely useful in studying and controlling the many diseases associated with protein variants.

Currently, studies to probe the mechanisms underlying these diseases and to develop appropriate therapeutic strategies have been greatly hampered because reagents that can selectively recognize specific protein variants are scarce. In order to address this critically important need, unique electric field-based methods have been developed to efficiently isolate and concentrate subtly different protein variants, and simultaneously developing novel biopanning methods to generate very selective molecular recognition reagents that can be used to identify specific disease related species and mechanisms.

To demonstrate the current technology, reagents were isolated that selectively bind a diverse array of different aggregate species of the protein amyloid-beta (Aβ ). While Aβ was first implicated in Alzheimer's Disease (AD) over 20 years ago the role of Aβ in AD is still unclear and has proven to be much more elusive than originally hoped. Much of the confusion around the role of Aβ in AD is due to the variety of different Aβ species that can occur in vivo. Aggregation of Aβ is a critically important though poorly understood factor in the progression of AD. While the amyloid plaques of AD contain fibrillar Aβ aggregates, a variety of other smaller aggregate species of Aβ can also be formed and increasing evidence implicates various small soluble oligomeric Aβ species in neurotoxicity and loss of synaptic function. Cortical levels of soluble Aβ correlate well with cognitive impairment and loss of synaptic function. Small soluble aggregates of Aβ, termed Aβ-derived diffusible ligands (ADDLs), and spherical or annular aggregates termed protofibrils were shown to be neurotoxic. Oligomeric forms of Aβ, created in vitro or derived from cell cultures, were shown to inhibit long term potentiation. The concentration of oligomeric forms of Aβ is also elevated in transgenic mouse models of AD and in AD brain. Disruption of neural connections was shown to occur near Aβ plaques and fibrils, suggesting a toxic role for the fibrillar form, however the disruption also occurred in regions without fibrillar Aβ deposition suggesting that the toxicity may be due to small amounts of oligomeric Aβ, some in equilibrium with the fibrillar form, some existing on their own. A halo of oligomeric Aβ was shown to surround Aβ plaques and correlate with synapse loss. Oligomeric Aβ was also shown to disrupt cognitive function in transgenic animal models of AD.

A major barrier impeding studies of the connection between Aβ and AD is the lack of suitable reagents to identify and localize the different Aβ species. Antibodies to selected Aβ forms have been previously generated by immunization methods using for example soluble oligomeric Aβ (Lambert, M. P., et al., Vaccination with soluble Abeta oligomers generates toxicity-neutralizing antibodies. J Neurochem, 2001. 79: p. 595-605) or molecular mimics of oligomeric Aβ (Kayed, R., et al., Common structure of soluble amyloid oligomers implies common mechanism of pathogenesis. Science, 2003. 300: p. 486-9). These reagents have been useful to demonstrate the importance of oligomeric Aβ in AD for example by confirming the presence of oligomeric Aβ in AD brains, showing they target synaptic ligands and bind strongly to neuronal dendrites, and that oligomeric Aβ correlates with synapse loss near amyloid plaques. However, while the current pool of reagents has been useful in pointing out the importance of soluble Aβ aggregates, their binding specificities are generally not well characterized, the affinities and specificities of the reagents are not sufficient to identify the presence of specific oligomeric species or of low concentration species and are not generally suitable for precise histochemical studies or to localize species to specific cellular locations in situ or in vivo. In addition, they are not suitable for intracellular studies.

Since soluble aggregates of Aβ, α-synuclein (α-syn) and tau have all been associated with neurodegenerative diseases, reagents that can recognize specific morphologies of specific proteins are needed to elucidate the roles of the different forms of these proteins in disease. Therefore there is a critical need for well characterized reagents that recognize specific Aβ forms to facilitate studies on the role of Aβ aggregation in AD, to identify the relevant toxic Aβ species, and to clarify where and when aggregation of Aβ begins and how it progresses in AD. This information is vitally important to understand the mechanism of AD, to facilitate diagnoses, and to develop appropriate markers for monitoring therapeutic interventions. Similar reagents are needed to probe the role of protein variants in other significant human diseases such as Parkinson's, diabetes, and cancer.

To address this need, novel techniques have been developed to separate and purify subtle protein variants and to generate and characterize reagents that recognize specific protein forms. To demonstrate the capabilities of the present technology to generate reagents to specific protein variants, protocols are modified so that the various in vitro generated Aβ species are separated. These conditions are used to separate the much more complex Aβ pool present in AD brain.

Subtle protein variants including alternatively processed and folded forms play critical roles in numerous human diseases, many of which cannot be distinguished by genomic and proteomic techniques. Despite the growing importance of protein variants in human disease, few tools are available to study and treat these phenomena because of the difficulty in identifying individual protein isoforms. Since there are often only subtle differences between protein variants, and many may be present only at trace levels or may not be particularly stable, isolating individual protein variants and generating reagents that selectively recognize each form are extremely challenging problems. To overcome these difficulties, protocols have been developed that enable the isolation and concentration of specific protein variant forms, and the generation of reagents that selectively bind specific protein variants using only trace amounts of target.

DC-iGDEP Separation Devices and Methods

One aspect of the present work utilizes the unique abilities of dielectrophoretic (DEP) and electrokinetic (EK) forces to separate protein isoforms. DEP forces typically are used to bifurcate particle systems or uniquely capture specific targets in areas of high gradient (or low gradient, negative versus positive DEP). The approach described herein uniquely harnesses these forces to form a separation scheme not unlike isoelectric focusing (IEF), in that an overarching gradient is formed and specific targets localize according to their unique properties: pI in the case of IEF and DEP/EK force balances in the case of DC-iGDEP. A local electric field gradient can be formed with insulating structures using a static electric field applied from electrodes located in remote inlet and outlet reservoirs (Cummings, E. B. and A. K. Singh, Dielectrophoresis in Microchips Containing Arrays of Insulating Posts: Theoretical and Experimental Results. Anal. Chem., 2003. 75: p. 4724-4731; Cummings, E. B., Streaming Dielectrophoresis for Continuous-Flow Microfluidic Devices. IEEE Engineering in Medicine and Biology Magazine, 2003. November/December: p. 75-84; Lapizco-Encinas, B. H., et al., Insulator-based dielectrophoresis for the selective concentration and separation of live bacteria in water. Electrophoresis, 2004. 25: p. 1695-1704; Lapizco-Encinas, B. H., et al., Dielectrophoretic Concentration and Separation of Live and Dead Bacteria in an Array of Insulators. Anal. Chem., 2004. 76: p. 1571-1579; Barrett, L. M., et al., Dielectrophoretic manipulation of particles and cells using insulating ridges in faceted prism microchannels. Analytical Chemistry, 2005. 77: p. 6798-6804; Lapizco-Encinas, B. H., et al., An insulator-based (electrodeless) dielectrophoretic concentrator for microbes in water. Journal of Microbiological Methods, 2005. 62: p. 317-326; Simmons, B. A., et al., The development of polymeric devices as dielectrophoretic separators and concentrators. MRS Bulletin, 2006. 31: p. 120-124; Davalos, R. V., et al., Performance impact of dynamic surface coatings on polymeric insulator-based dielectrophoretic particle separators. Analytical and Bioanalytical Chemistry, 2008. 390: p. 847-855).

The present method adds a global gradient to the system, allowing the longitudinal separation of mixtures as opposed to a simple bifurcation of two components (Pysher, M. D. and M. A. Hayes, Electrophoretic and dielectrophoretic field gradient technique for separating bioparticles. Analytical Chemistry, 2007. 79: p. 4552-4557; Chen, K. P., et al., Insulator-based Dielectrophoretic Separations of Small Particles in Sawtooth Channel. Electrophoresis, 2009. 30: p. 1441-1448; Jones, P. V., S. J. R. Staton, and M. A. Hayes, Blood Cell Capture in a Gradient Dielectrophoretic Microchannel. Anal. Bioanal. 2011. 401: p. 2103-2111; Staton, S. J. R., et al., Characterization of particle capture in a sawtooth patterned insulating electrokinetic microfluidic device. Electrophoresis, 2010. 31: p. 3634-3641; Weiss, N. G., et al., Dielectrophoretic mobility determination in DC insulator-based dielectrophoresis. Electrophoresis, 2011. 32, 2292-2297; Staton, S. R., et al., Gradient Insulator Based Dielectrophoresis Isolation and Concentration of A-beta Amyloid Fibrils. Analyst, 2012. 137, in press (RSC ID: AN-COM-01-2012-035138)).

The insulating structures are fabricated such that an increasing local gradient is induced along the length of a microfluidic channel (FIG. 1). This sawtooth structure enables separations to be based on high multipole moments. Generally, simple electrophoresis accesses the monopole electric properties of a molecule or particle. For complex molecules and bioparticles, several intricate electrical geometries exist which can be used for separation (see for ex. Jones, T. B. and M. Washizu, Generalized multipolar dielectrophoretic force and electrorotational torque calculation. Journal of Electrostatics, 1996. 38: p. 199-211). Protocols have been developed to gently (cells remain viable) separate several targets along a gradient based on specific features of each target. These features can be as subtle as deformability or as simple as size. In addition to earlier work focused on model particles, several species of bacteria and cells from whole human blood have been isolated (along with a model in support of the present work (Chen, K. P., et al., Insulator-based Dielectrophoretic Separations of Small Particles in Sawtooth Channel. Electrophoresis, 2009. 30: p. 1441-1448)), and it has been shown that different Aβ species can be uniquely captured. All devices used to generate these results were created with photolithographic templates fabricated with AZ P4620 photoresist (Pysher, M. D. and M. A. Hayes, Electrophoretic and dielectrophoretic field gradient technique for separating bioparticles. Analytical Chemistry, 2007. 79: p. 4552-4557).

The basic approach is demonstrated with polystyrene particles varying in size from 20 nm to 1 micron in diameter being isolated along the increasing gradient (Staton, S. J. R., et al., Characterization of particle capture in a sawtooth patterned insulating electrokinetic microfluidic device. Electrophoresis, 2010. 31: p. 3634-3641). The small space between the tips of the insulating structures (gates) on the narrowest portion of the device do not clog, consistent with the inventors' modeling studies showing that the particles never actually penetrate the narrowest zone (Chen, K. P., et al., Insulator-based Dielectrophoretic Separations of Small Particles in Sawtooth Channel. Electrophoresis, 2009. 30: p. 1441-1448). Differential behaviors were observed for two populations of the same sized particles, indicating that dielectrophoretic forces act on factors beyond just size—perhaps heterogeneous permittivity (Staton, S. J. R., et al., Characterization of particle capture in a sawtooth patterned insulating electrokinetic microfluidic device. Electrophoresis, 2010. 31: p. 3634-3641). Live and dead bacteria were easily separated using this setup without clogging, verifying the modeled behavior of the micro and nano particles (Pysher, M. D. and M. A. Hayes, Electrophoretic and dielectrophoretic field gradient technique for separating bioparticles. Analytical Chemistry, 2007. 79: p. 4552-4557). It was also possible to separate red blood cells (RBCs) from other types of cell debris or proteins (Blood Cell Capture in a Gradient Dielectrophoretic Microchannel. Anal. Bioanal. 2011. 401: p. 2103-2111). A component of this system has also been modeled, which was a series of seven tooth pairs that do not converge and no particle-particle interactions are included (Chen, K. P., et al., Insulator-based Dielectrophoretic Separations of Small Particles in Sawtooth Channel. Electrophoresis, 2009. 30: p. 1441-1448). Using just these limiting constraints the ratio of electrokinetic forces (electrophoretic and electroosmotic, $\mu_{ep}+\mu_{eof}$ mobilities) and dielectrophoretic forces was shown to be unique at each gate. The shape of the projected electric field and resulting field gradient is strongly influenced by the shape of the insulators.

Development of DC-iGDEP Device to Isolate a Full Range of In Vitro Generated Aβ Species.

The unique capabilities of DC-iGDEP are used to extend the production of nanobodies to create a suite of precise probes of Aβ aggregates specific to AD patients. To accomplish this, a DC-iGDEP device is fabricated that maximizes resolution of the Aβ aggregate species ranging from dimers to full fibrils, including metastable (several minutes timescale) intermediates. The location within the DC-iGDEP device of selected isolated and concentrated Aβ40 and 42 aggregate species is confirmed, exploiting existing nanobodies with precise affinity for various protein regions and morphologies.

Separation results have been obtained using the open channel sawtooth design on a variety of systems including different size polystyrene particles (Staton, S. J. R., et al., Characterization of particle capture in a sawtooth patterned insulating electrokinetic microfluidic device. Electrophoresis, 2010. 31: p. 3634-3641), red blood cells (Blood Cell Capture in a Gradient Dielectrophoretic Microchannel. Anal. Bioanal. 2011. 401: p. 2103-2111), and bacteria (Pysher, M. D. and M. A. Hayes, Electrophoretic and dielectrophoretic field gradient technique for separating bioparticles. Analytical Chemistry, 2007. 79: p. 4552-4557), and have developed a theoretical model to predict separation properties (Chen, K. P., et al., Insulator-based Dielectrophoretic Separations of Small Particles in Sawtooth Channel. Electrophoresis, 2009. 30: p. 1441-1448).

The inventors have also shown that the design can isolate and concentrate fully formed Aβ fibrils while allowing monomers to pass freely (FIG. 1). In this design, the Aβ fibrils were captured at a "gate" (closest approach of the insulating teeth) with a 27 micron spacing, resulting in a squared field strength gradient calculated (COMSOL multiphysics) to be approximately $10^{18}$ $V^2/m^3$. These results were obtained within 5-15 minutes after loading the device with approximately 40 microliters of the monomer or fibril solution/colloid. The data demonstrate that this unique separation scheme is well controlled and is ideally suited for the selective isolation and concentration of aggregation intermediates.

According to the basic accepted theories underlying DEP and EK, the net velocity of a particle/molecule is proportional to particle radius (a) squared [$v_{DEP}=\mu_{DEP}\nabla E^2$, $\mu_{DEP}\propto\alpha^2$: $v_{DEP}$ is the velocity of a particle due to DEP forces and E is the local electric field (Chen, K. P., et al., Insulator-based Dielectrophoretic Separations of Small Particles in Sawtooth Channel. Electrophoresis, 2009. 30: p. 1441-1448;

Weiss, N. G., et al., Dielectrophoretic mobility determination in DC insulator-based dielectrophoresis. Electrophoresis, 2011. 32, 2292-2297)]. Using this relationship and noting that monomeric Aβ nominally are about 1.5 nanometers across and the characteristic of length of fibrils is in the 10s to 100s of nanometers (Roychaudhuri, R., et al., Amyloid beta-Protein Assembly and Alzheimer Disease. Journal Of Biological Chemistry, 2009. 284: p. 4749-4753), the range of expected DEP forces needed is effectively bracketed [estimate E, $\Delta E^2$ from COMSOL, use Aβ (1-40) monomer $\mu_{EP}$ (10.0 mM TRIS buffer, pH 7.8) of $1.20\times10^4$ $cm^2/V$ s and Aβ (1-42) monomer $\mu_{EP}$ (10.0 mM TRIES buffer, pH 7.8) is $1.072\times10^4$ $cm^2/V$ s (about four peak widths difference between Aβ 40 and 42) (Picou, R., et al., Analysis of monomeric A beta (1-40) peptide by capillary electrophoresis. Analyst, 2010. 135: p. 1631-1635; Picou, R. A., et al., Analysis of A-beta (1-40) and A-beta (1-42) Monomer and Fibrils by Capillary Electrophoresis. Journal of Chromatography B, 2011DOI: 10.1016/j.jchromb.2011.01.030)]. A device with the "gate" spacing starting at 50 microns and decreasing over two centimeters to 1 micron effectively captures, at varying points, Aβ species ranging from monomers to fibrils (FIG. 1, bottom graphic). COMSOL multiphysics was used to design these devices, and the resulting underlying structures are transferred to AutoCAD for creation of photolithographic plates.

With this design, various Aβ aggregates are separated, although not homogeneously (evenly spaced or uniquely isolated), ranging from monomers to fully formed fibrils. This takes place in a matter of minutes as a typical velocity (EP only, open portions of the device) is $\sim10^{-4}$ m/s. Further, compared to the loading volume of approximately 50 microliters, specific targets can be concentrated by several orders of magnitude (up $10^6$).

Figure 3:
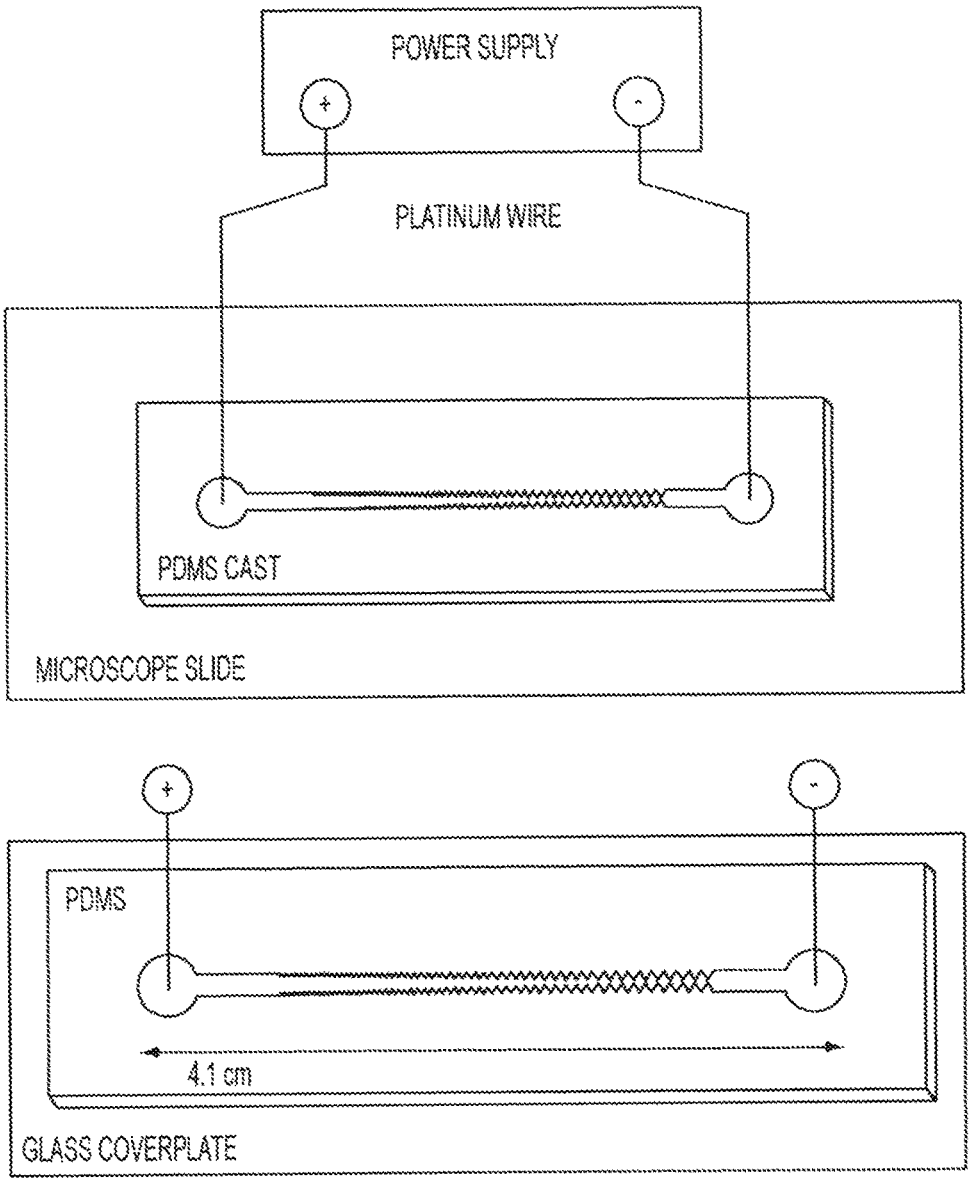
FIG. 3 depicts an embodiment of the present device. Diagram of the direct current insulator gradient dielectrophoresis (DC-iGDEP) device. An insulated sawtooth pattern is integrated with a tapered microfluidic channel to generate localized non-uniform electric field gradients of increasing strength from left to right.

Device:

Microchannel geometry consisted of sets of successively larger, equilateral triangular features lining both sides of the channel (FIG. 3). The tip of each triangle corresponded with another opposing triangle on the other side of the channel, forming sequentially narrower gaps along a converging sawtooth pattern. The smallest triangles (located near the entrance to the channel) possessed 6-μm sides and a 5.2-μm height. The side-length of the equilateral triangles increased by 40 μm after every sixth repeated unit. This created a channel with an initial gap pitch of 945 μm and a final gap pitch of 27 μm. The whole channel length was approximately 4.1 cm with an average depth of 14±1 μm.

Materials and Methods:

Microfluidic devices constructed from both glass and polydimethylsiloxane (PDMS) were used to perform the experiments. Platinum electrodes were inserted through small access ports into reservoirs at each end of the microchannel and used to apply potential across the device.

PDMS (Sylgard 184, Dow/Corning, Midland, Mich.) was poured over a photoresist template patterned on a silicon wafer and allowed to cure. Two-millimeter diameter holes were punched through the PDMS at each end of the channel to access the reservoirs. The PDMS, along with a glass slide, were then oxidized via oxygen-plasma treatment and then irreversibly bonded.

Cell samples were typically collected in phosphate buffer and fluorescently stained to aid visualization during experiments (Vybrant DiO, Invitrogen, Inc., Carlsbad, Calif.).

Buffer was pipetted into the inlet reservoir, causing the channel to fill passively via capillary action. After inspecting the device and ensuring uniform fluid distribution, sample was then pipetted into the inlet reservoir. After analyte bioparticles had entered the device via pressure-driven flow and attained uniform distribution within the channel, buffer was added to the opposite reservoir in order to balance the hydrodynamic pressure. Once the device was prepared in this manner, platinum electrodes (0.404 mm external diameter 99.9% purity, Alfa Aesar, Ward Hill, Mass.) were inserted through the access ports into the reservoirs and connected to a Series 225 DC power supply (Bertan High Voltage Corp., Hicksville, N.Y.). Experiments were observed with an Olympus IX70 microscope. Samples were illuminated using a broad-spectrum mercury lamp (H30 102 w/2, OSRAM) and an Olympus DAPI, FITC, Texas Red triple band-pass cube (Olympus, Center Valley, Pa.).

Generation of Nanobodies.

The inventors have developed novel technology enabling the generation of reagents that recognize specific protein conformations by combining the powerful imaging capabilities of Atomic Force Microscopy (AFM) with the molecular recognition diversity of phage display libraries (Barkhordarian, H., et al., Isolating recombinant antibodies against specific protein morphologies using atomic force microscopy and phage display technologies. Protein Eng Des Sel, 2006. 19: p. 497-502; Shlyakhtenko, L. S., et al., Single-molecule selection and recovery of structure-specific antibodies using atomic force microscopy. Nanomedicine, 2007. 3: p. 192-7). The inventors have also developed innovative technologies that allow the characterization of binding specificity of these reagents using only nanograms of material again utilizing AFM (Wang, M. S., et al., Characterizing Antibody Specificity to Different Protein Morphologies by AFM. Langmuir, 2008). In order to isolate single chain antibody fragments (or nanobodies) to individual aggregate forms, an AFM biopanning technology was developed that allows the visualization of the target protein morphology (Barkhordarian, H., et al., Isolating recombinant antibodies against specific protein morphologies using atomic force microscopy and phage display technologies. Protein Eng Des Sel, 2006. 19: p. 497-502; PCT/US11/57887; PCT/US11/57925; PCT/US11/57904).

The protocol is particularly well suited to isolate nanobodies against different protein morphologies since it minimizes protein handling, as the target protein is added to the mica surface without modification, it uses small amounts of protein, low nanogram quantities are more than sufficient, and the target protein does not have to be purified. This basic technology ahs been utilized to isolate nanobodies that recognize different areas of monomeric Aβ and a-syn (Emadi, S., et al, Inhibiting Aggregation of alpha-Synuclein with Human Single Chain Antibody Fragments. Biochemistry, 2004. 43: p. 2871-2878; Zhou, C., et al., A human single-chain Fv intrabody blocks aberrant cellular effects of overexpressed alpha-synuclein. Mol Ther, 2004. 10: p. 1023-31; Liu, R., et al., Single chain variable fragments against beta-amyloid (Abeta) can inhibit Abeta aggregation and prevent abeta-induced neurotoxicity. Biochemistry, 2004. 43: p. 6959-67; Zameer, A., et al., Single Chain Fv Antibodies against the 25-35 Abeta Fragment Inhibit Aggregation and Toxicity of Abeta42. Biochemistry, 2006. 45: p. 11532-9), fibrillar Aβ and a-syn (Barkhordarian, H., et al., Isolating recombinant antibodies against specific protein morphologies using atomic force microscopy and phage display technologies. Protein Eng Des Sel, 2006. 19: p. 497-502; Marcus, W. D., et al., Characterization of an antibody scFv that recognizes fibrillar insulin and beta-amyloid using atomic force microscopy. Nanomedicine, 2008. 4: p. 1-7), two different oligomeric α-syn species (Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58), and three different oligomeric Aβ species (Zameer, A., et al., Anti-oligomeric Abeta single-chain variable domain antibody blocks Abeta-induced toxicity against human neuroblastoma cells. J Mol Biol, 2008. 384: p. 917-28; Kasturirangan, S., et al., Nanobody specific for oligomeric beta-amyloid stabilizes non-toxic form. Neurobiol Aging, 2010. In press; Kasturirangan, S., et al., Isolation and Characterization of a Nanobody that Selectively Binds Brain Derived Oligomeric Beta-Amyloid. (Submitted)).

The different oligomer specific nanobodies do not show cross-reactivity, so the nanobodies binding oligomeric Aβ do not bind oligomeric α-syn and vice versa. The nanobodies work well in standard ELISA and immunohistochemistry assays as it has been shown that each of the different aggregate species recognized by the different nanobodies naturally occur in human AD or PD tissue, and that the nanobodies can be used to distinguish between AD, PD and healthy brain tissue, and block toxicity of different aggregate species (Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Emadi, S., et al., Detecting morphologically distinct oligomeric forms of alpha-synuclein. J Biol Chem, 2009. 284: p. 11048-58; Zameer, A., et al., Anti-oligomeric Abeta single-chain variable domain antibody blocks Abeta-induced toxicity against human neuroblastoma cells. J Mol Biol, 2008. 384: p. 917-28; Kasturirangan, S., et al., Nanobody specific for oligomeric beta-amyloid stabilizes non-toxic form. Neurobiol Aging, 2010. In press). The nanobodies currently developed have several significant advantages over conventional antibodies including: 1) they target specific morphologies of a single protein target for example recognizing a selected Aβ oligomer form, but not any α-syn oligomer forms, 2) they can be affinity matured to femtomolar levels; 3) they can be genetically modified with targeting or tag sequences; 4) they can be expressed intracellularly as intrabodies to identify intracellular Aβ species; and 5) their specificities can be carefully characterized.

Combination of the novel separation and molecular recognition technologies enables the ability to identify and concentrate specific protein isoforms connected with diseased human tissue and to generate nanobody reagents that selectively recognize the different protein isoforms characteristic of the disease. The resulting panel of nanobodies provide extremely powerful tools in this case for the AD community to better define the roles of the different Aβ species in the progression of AD. This effort provides a clear and immediately useful example of the overall strategy of highly refined reagent development.

In certain embodiments, the antibody fragments that can be used in the present invention are those listed in Table 1 below (See also FIG. 2):

TABLE 1

| Antibody Fragment | Library source | Specificity | Assays to validate | Applications demonstrated | SEQ ID NO |
|---|---|---|---|---|---|
| A4 | Tomlinson (MRC) | Oligomeric Abeta 3-day aggregates | Dot blot, time course, ELISA, AFM (Note: 3-day oligomeric target is not stable for westerns) | Human AD brain tissue, Human CSF, Mouse AD brain tissue, (Dot blot assays). Immunohistochemistry | amino acid SEQ ID NO: 2; nucleic acid SEQ ID NO: 8 |
| E1 | Tomlinson (MRC) | Oligomeric Abeta 1-day aggregates | Dot blot, time course, ELISA, AFM (Note: 1-day oligomeric target is not stable for westerns) | Human AD brain tissue, Human CSF, Mouse AD brain tissue, (Dot blot assays) | amino acid SEQ ID NO: 3; nucleic acid SEQ ID NO: 9 |
| C6 | Sheets (UCSF) | Oligomeric Abeta: brain derived | AFM | Human AD brain tissue, Human CSF, Mouse AD brain tissue, (Dot blot assays) | amino acid SEQ ID NO: 1; nucleic acid SEQ ID NO: 10 and amino acid SEQ ID NO: 15 |
| D5 | Tomlinson (MRC) | Oligomeric a-synuclein 3-day aggregates | Dot blot, time course, ELISA, AFM, western blot analysis | Human PD brain tissue, Human CSF, Mouse PD brain tissue, (Dot blot assays, western blot, Immunohistochemistry with tissue and cells | amino acid SEQ ID NO: 4; nucleic acid SEQ ID NO: 11 |

TABLE 1-continued

| Antibody Fragment | Library source | Specificity | Assays to validate | Applications demonstrated | SEQ ID NO |
|---|---|---|---|---|---|
| 10H | Tomlinson (MRC) | Oligomeric a-synuclein 7-day aggregates | Dot blot, time course, ELISA, AFM, western blot analysis | Human PD brain tissue, Mouse PD brain tissue, (Dot blot assays, western blot, Immunohistochemistry with tissue and cells | amino acid SEQ ID NO: 5; nucleic acid SEQ ID NO: 12 |
| 6E | Tomlinson (MRC) | Fibrillar aggregates (likely not protein specific) | Dot blot, time course, ELISA, AFM | Human PD brain tissue, Human CSF, Mouse PD brain tissue, (Dot blot assays, western blot, Immunohistochemistry with tissue and cells | amino acid SEQ ID NO: 6; nucleic acid SEQ ID NO: 13 |
| D10 | Tomlinson (MRC) | All forms of a-synuclein | Dot blot, time course, ELISA, AFM, western | Human PD brain tissue, Human CSF, Mouse PD brain tissue, (Dot blot assays, western blot, Immunohistochemistry with tissue and cells | amino acid SEQ ID NO: 7; nucleic acid SEQ ID NO: 14 |
| BSEC1 | PNRL (Pacific National Research Labs?) Yeast library | BACE1 cleavage site on APP (Does not bind soluble Abeta | BACE-1 catalytic assay | Cell toxicity, cell culture assays | |

In certain embodiments, the C6 nanobody has a sequence of SEQ ID NO:1:

```
EXPIAYGSRWIVITRGPAGHGPGTAAGVGGGLVQPGGSLRLSCAASGF
TFSSYAMSWVRQAPGKGLEWVSAISGSGGSTYYADSVKGRFTISRDNS
KNTLYLQMNSLRAEDTAVYYCAKSYGSVKISCFDYWGQSTLVTVSSG
GGGSGGGGSGGGGSEIVLTQSPDSLAVSLGERATINCKSSQSVLYNSN
NKNYLAWYQQKPGQSPELLIYWASTRESGVPDRFSGSGSGTEFTLTISS
LQAEDVAVYYCQQFYSTPPTFGQGTKLEIKRAAAHHHHHHGAAEQKL
ISEED
```

In certain embodiments, the antibody fragment comprises amino acid residues 16-292 of SEQ ID NO:1. In certain embodiments, the antibody fragment comprises or consists of amino acid sequence SEQ ID NO:1. In certain embodiments, the antibody fragment is less than 500 amino acids in length, such as between 200-450 amino acids in length, or less than 300 amino acids in length.

Identification of Isolated Aβ40/42 Fractions that React with Existing Morphology-Specific Nanobodies.

Several different nanobodies to different Aβ morphologies including ones that selectively bind only fibrillar Aβ (Marcus, W. D., et al., Characterization of an antibody scFv that recognizes fibrillar insulin and beta-amyloid using atomic force microscopy. Nanomedicine, 2008. 4: p. 1-7) or three different oligomeric species of Aβ (Zameer, A., et al., Anti-oligomeric Abeta single-chain variable domain antibody blocks Abeta-induced toxicity against human neuroblastoma cells. J Mol Biol, 2008. 384: p. 917-28; Kasturirangan, S., et al., Nanobody specific for oligomeric beta-amyloid stabilizes non-toxic form. Neurobiol Aging, 2010. In press; Kasturirangan, S., et al., Isolation and Characterization of a Nanobody that Selectively Binds Brain Derived Oligomeric Beta-Amyloid. (Submitted)) have been developed by the inventors. This existing pool of morphology specific nanobodies is used to verify that distinct Aβ species are separated in the DC-iGEP protocols, and to identify novel Aβ species for which there are not selective reagents.

Separation and Collection of Aβ Fractions.

Aβ fractions are isolated and concentrated along the sawtooth gates. Each Aβ fraction is captured within the so called "cell" (the area between the gates) (Staton, S. J. R., et al., Characterization of particle capture in a sawtooth patterned insulating electrokinetic microfluidic device. Electrophoresis, 2010. 31: p. 3634-3641). An additional design feature is needed to keep the collected targets within a confined volume, yet accessible to various reagents. Lateral channels are used that are "electrically silent" when the electric field is placed across the long axis of the device. By placing electrodes in reservoirs placed above and below the device and corresponding channels, the captured Aβ species for subsequent analysis is recovered.

Reactivity of Aβ Fractions with Nanobody.

There are numerous techniques that are used to determine binding specificity of each of the nanobodies isolated against the different target Aβ morphologies depending on the availability and stability of the target antigen. In characterizing binding specificity to the different Aβ species isolated by DC-iGDEP, most Aβ species are present in only very small amounts and low volume. For these cases, reactivity of the existing species is analyzed using AFM, which utilizes minimal material without the need for any modification. For those Aβ morphologies that are obtained in reasonable quantity, binding specificity is determined by ELISA, western or dot blot, depending on how easy it is to purify the target aggregate morphology. The protocols for each of these assays are routinely used (Emadi, S., et al., Inhibiting Aggregation of alpha-Synuclein with Human Single Chain Antibody Fragments. Biochemistry, 2004. 43: p. 2871-2878; Zhou, C., et al., A human single-chain Fv intrabody blocks aberrant cellular effects of overexpressed alpha-synuclein. Mol Ther, 2004. 10: p. 1023-31; Liu, R., et al., Single chain variable fragments against beta-amyloid (Abeta) can inhibit Abeta aggregation and prevent abeta-induced neurotoxicity. Biochemistry, 2004. 43: p. 6959-67; Zameer, A., et al., Single Chain Fv Antibodies against the 25-35 Abeta Fragment Inhibit Aggregation and Toxicity of Abeta42. Biochemistry, 2006. 45: p. 11532-9; Emadi, S., et al., Isolation of a human single chain antibody fragment against oligomeric alpha-synuclein that inhibits aggregation and prevents alpha-synuclein-induced toxicity. J Mol Biol, 2007. 368: p. 1132-44; Liu, R., et al., Residues 17-20 and 30-35 of beta-amyloid play critical roles in aggregation. J Neurosci Res, 2004. 75: p. 162-71; Liu, R., et al., Proteolytic antibody light chains alter beta-amyloid aggregation and prevent cytotoxicity. Biochemistry, 2004. 43: p. 9999-10007). In certain circumstances, the nanobody specificity for some of the oligomeric Aβ samples may not be able to determined by conventional means such as western blot as described above. Several different AFM based methods are used to determine antibody specificity for antigen targets that are not suitable for analysis as described above, or that are available in only limited amounts. For example, nanobody specificity by height distribution analysis (Wang, M. S., et al., Characterizing Antibody Specificity to Different Protein Morphologies by AFM. Langmuir, 2008) or by recognition imaging (Marcus, W. D., et al., Isolation of an scFv targeting BRG1 using phage display with characterization by AFM. Biochem Biophys Res Commun, 2006. 342: p. 1123-9).

At least five Aβ fractions are separated, including monomeric, several oligomeric and a fibrillar form. In certain situation if the lateral channels are not sufficiently electrically silent or they are accessible under the diffusive conditions during processing, a simple pneumatic valve concept is used (Unger, M. A., et al., Monolithic microfabricated valves and pumps by multilayer soft lithography. Science, 2000. 288: p. 113-116), where the roof of the lateral channels are closed by applying pressure because the device is made of elastic polymers. Pressure is nominal, and can be applied mechanically.

The invention will now be illustrated by the following non-limiting Examples.

Example 1

Here we report a novel method for the manipulation and concentration of Aβ amyloid fibrils, implicated in Alzheimer's disease, using DC insulating gradient dielectrophoresis (DC-iGDEP). Fibril enrichment was found to be ~400%. Simulations suggest that capture of the full range of amyloid protein aggregates is possible with optimized device design.

Protein aggregates have been associated with more than 25 human diseases, including Alzheimer's disease, Parkinson's disease and type 2 diabetes. As a result, researchers in medical, biochemical and analytical chemistry fields are striving to understand the mechanisms of formation of amyloid aggregates and to identify toxic species. Protofibrils, transient metastable oligomeric aggregates that develop prior to the formation of amyloid fibrils, have been implicated in disease pathogenesis and are considered to be cytotoxic. Amyloid aggregation has been shown to form a heterogeneous mixture of oligomeric species in vitro, but the specific structure or structures of the cytotoxic species, their relationship to amyloid fibril formation and the mechanism of toxicity are unknown. Techniques capable of manipulating and concentrating various aggregate structures are of paramount importance because specific knowledge of all constituent aggregate species is needed to effectively develop therapeutics based on disrupting or altering the aggregation process. Each of the different aggregate species from monomer to mature fibrils can have unique chemical and physical properties providing a basis for differential toxicity.

Traditional means of isolating various oligomers and fibrils of Aβ amyloid and other misfolded proteins have relied heavily on techniques such as sedimentation, size-exclusion chromatography (SEC) and capillary electrophoresis (CE). Sedimentation typically uses large volume preparations and cannot effectively separate oligomers into subpopulations, given their structural similarities and the typical small volumes of aggregate samples. While CE uses small volume samples and provides greater resolution compared to other separation techniques, target populations generally are diluted rather than concentrated during separation. Similarly, SEC has proven effective for isolating relatively stable protofibril species, but as with CE, samples are generally diluted during separation, and it has been shown to disrupt some protein aggregates. Several other methods used to isolate and characterize Aβ aggregates include HPLC, gel electrophoresis, and transmission electron microscopy (TEM); however, these methods do not provide a comprehensive account of the coexisting oligomeric populations during amyloid fibril formation. TEM measurements are made after extensive sample preparation and generally only capture stable end-point species. Considering amyloid fibril formation as a series of reversible reactions suggests that all separation schemes can alter the populations of aggregate species present before separation. For instance, protofibrils can convert back to monomers. To provide the most realistic view of the population of aggregates in a sample, a separation-based technique should be as rapid and gentle as possible.

The technique described here, direct current based insulator gradient dielectrophoresis (DC-iGDEP), rapidly resolves particulates by balancing electrophoresis and dielectrophoresis within a single separation channel. (S. J. R. Staton, K. P. Chen, T. J. Taylor, J. R. Pacheco and M. A. Hayes, Electrophoresis, 2010, 31, 3634-3641.) Relative to a capillary electrophoretic separation, the addition of dielectrophoretic forces increases the analyte-specific separation vectors to include the permeability and conductivity of the particle as well as the same parameters for the surrounding medium, which can be tuned. Combining these forces in opposition translates into discrete collection points that also concentrate the target species. This achieves both the separation and concentration of Aβ amyloid structures in a short time frame for direct quantification or use in downstream research on the properties of those structures. The separation is not based on the interaction of the aggregates with a stationary phase, reducing the impact of the separation process on the aggregate structures.

Previously, it has been demonstrated that DC-iGDEP can separate and concentrate spherical synthetic polymer nano- and microparticles from 20 nm to 1 μm. (S. J. R. Staton, K. P. Chen, T. J. Taylor, J. R. Pacheco and M. A. Hayes, Electrophoresis, 2010, 31, 3634-3641; M. D. Pysher and M. A. Hayes, Anal. Chem. 2007, 79, 4552-4557.) It was not known if DCiGDEP could be used successfully to manipulate species with the size, shape and chemical properties of amyloid aggregates. Here we present initial studies demonstrating that DC-iGDEP is able to rapidly and selectively concentrate Aβ amyloid aggregates, and has the potential to analyze populations of smaller protofibrillar aggregates with further tailoring of the channel design.

The design and fabrication of the DC-iGDEP device is detailed in Staton et al. (S. J. R. Staton, K. P. Chen, T. J. Taylor, J. R. Pacheco and M. A. Hayes, Electrophoresis, 2010, 31, 3634-3641) Briefly, the DC-iGDEP microfluidic channel was fabricated in polydimethylsiloxane (PDMS) with a glass cover slide (FIG. 3), and 20 μL of Aβ sample was introduced into the reservoir at the broader end of the channel. The Aβ monomer and fibrils in PBS were prepared as described in detail previously. (B. O'Nuallain, A. K. Thakur, A. D. Williams, A. M. Bhattacharyya, S. Chen, T. Geetha and R. Wetzel, Methods Enzymol., 2006, 413, 34-74; R. Picou, J. P. Moses, A. D. Wellman, I. Kheterpal and S. D. Gilman, Analyst, 2010, 135, 1631-1635; I. Kheterpal, K. D. Cook and R. Wetzel, Methods Enzymol. 2006, 39, 584-593; R. A. Picou, I. Kheterpal, A. D. Wellman, M Minnamreddy, G. Ku and S. D. Gilman, J. Chromatogr. B, 2011, 879, 627-632.) Additional information about the fabrication of the DC-iGDEP and Aβ sample preparation can be found in Example 2. The monomer and fibril samples were tested separately by DC-iGDEP. The results reported here were consistent and representative of multiple experiments using three independent preparations of the monomer and fibrils and multiple devices. Experiments were performed by applying voltages between 400 to 1000 V (over the entire channel length) for 1 to 15 min for each experiment.

Figure 4:
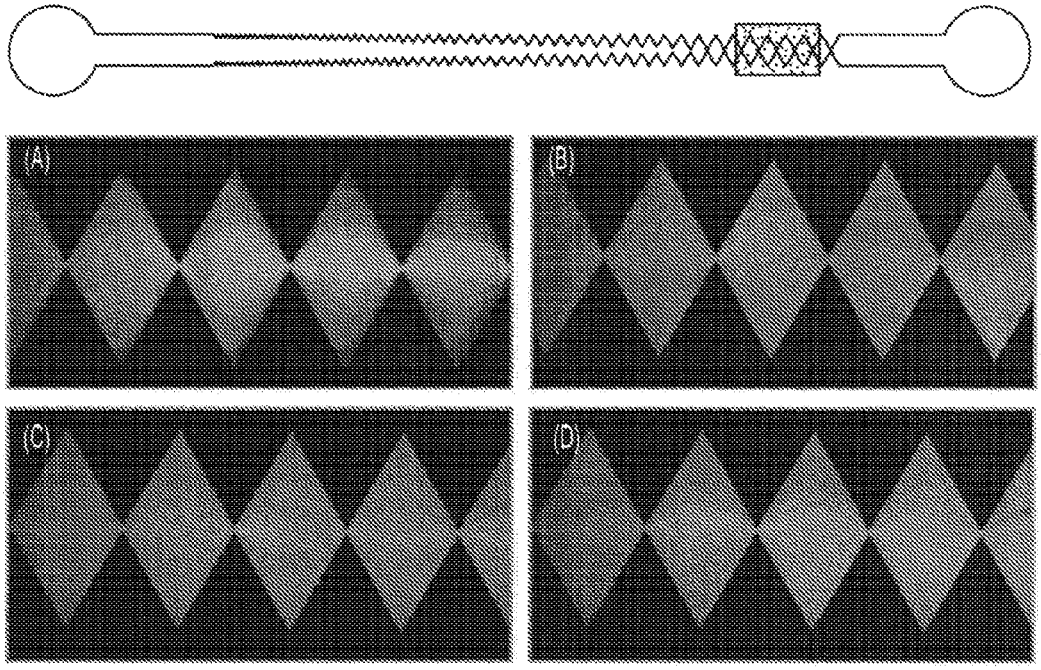
FIGS. 4A-4D. Fluorescence images of the narrowest portion of the DC-iGDEP for Aβ monomer samples (30 μM) with (A) 400 V, (B) 600 V, (C) 800 V, and (D) 1000 V applied. The diffuse light areas show the fluorescently tagged Aβ monomer distributed throughout the channel. Streaming of monomer is more visually apparent in (C) and (D).

The DC-iGDEP experiments were monitored by fluorescence microscopy. When introduced into the DC-iGDEP channel, the monomer consistently created streaming patterns at all of the applied voltages (400 to 1000 V, FIG. 4), which were more apparent at higher voltages. The streamlines appearing along the centerline of the channel indicate significant influence of electrophoretic forces; however, none of the conditions tested resulted in the monomers being captured.

Figure 5:
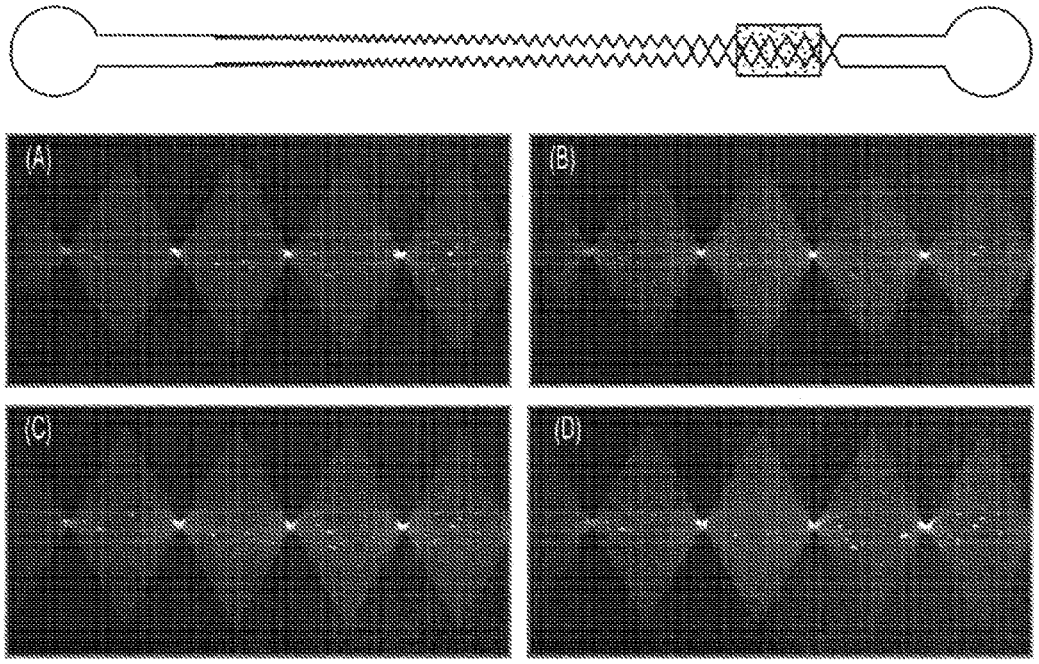
FIG. 5A-5D. Fluorescence images of the narrowest portion of the DCiGDEP (same as in FIG. 4) showing capture of Aβ fibrils (30 μM) at (A) 400 V, (B) 600 V, (C) 800 V, and (D) 1000 V applied. The areas of high fluorescence localized between the tips of the sawtooth patterned insulator indicate small zones where the fibrils were captured and concentrated.
Figure 6:
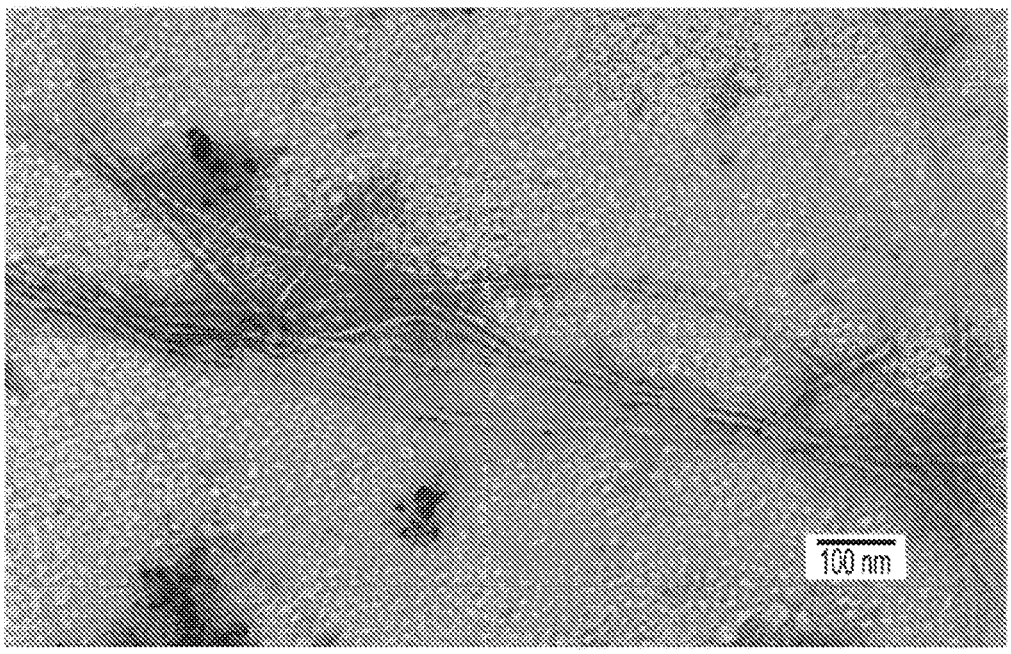
FIG. 6. TEM of the mature Aβ fibrils used in FIG. 5. The scale bar is 100 nm, and the fibril sample was in PBS before buffer exchange to Tris.

In contrast, when the Aβ amyloid fibril samples were tested using the DC-iGDEP channel under similar conditions, separation and concentration of the fibrils were observed (FIG. 5). A TEM of the fibril sample used in this experiment is presented in FIG. 6 and clearly shows the presence of mature amyloid fibrils. Thioflavin T (10 μM) fluorescence measured that aggregation was complete after 7 days. Images of experiments below 400 V applied over the length of the channel indicated movement of fibrils without capture. At 400-1000 V applied, the Aβ fibrils were captured and concentrated at the narrow points in the channel with similar local fluorescence intensity. Previous studies with synthetic nanospheres have demonstrated that particle capture typically does not obstruct the channels, and nanoparticles below the capture threshold size will pass through an intersection containing larger particles that have been concentrated and captured. (S. J. R. Staton, K. P. Chen, T. J. Taylor, J. R. Pacheco and M. A. Hayes, Electrophoresis, 2010, 31, 3634-3641.)

In order to differentiate between nonspecific and DC-iGDEP controlled capture, the applied voltage was removed after the capture and concentration of Aβ fibrils, and bright areas were monitored for dispersion away from the capture area. The bright fluorescence regions shown in FIG. 5 rapidly dissipated due to diffusion and slight convection of the Aβ fibrils away from the capture regions. Following a short period of time, the voltage was reapplied to allow selective capture to occur again. This process was repeated several times to verify that the capture was the result of the DC-iGDEP as well as to demonstrate the ability of the technique to reproducibly manipulate the amyloid aggregates within a given experimental session. The fibrils controllably collected near tips of the sawtooth-patterned insulating channel. The position of capture indicates that, under these experimental conditions, the fibrils exhibited properties consistent with positive dielectrophoresis, meaning that the collection points were where the electric field intensity is greatest. (S. J. R. Staton, K. P. Chen, T. J. Taylor, J. R. Pacheco and M. A. Hayes, Electrophoresis, 2010, 31, 3634-3641; H. A. Pohl, Dielectrophoresis, Cambridge University Press, 5 Cambridge, 1978; K. P. Chen, J. R. Pacheco, M. A. Hayes and S. J. R. Staton, Electrophoresis, 2009, 30, 1441-1448.) According to classic theory, particles that undergo positive dielectrophoretic capture are less permeable than the surrounding medium. Some evidence of nonspecific adsorption of the amyloid aggregates was observed along the channel surface. Without surface treatments or coatings nonspecific protein adsorption is common for PDMS channels.

The ability of the DC-iGDEP method to concentrate fibrils was examined semi-quantitatively by noting the fluorescence intensity at the collection points compared to background levels in the channel prior to collection and areas where no detectable capture had occurred. The resulting enrichment of the fibril material ranged from about 350% to over 500% depending on the applied voltage (see Example 2). However, under more ideal conditions with lower fibril loads, the potential capture efficiency could be as high as 600%, simply by reducing the amount of background fluorescence. The maximum observed enrichment was 520% at 600 V.

The overall goal of this work is to separate, capture and concentrate the full range of aggregate structures generated during mature amyloid fibril formation. The experimental results presented here demonstrate that mature Aβ fibrils, but not Aβ monomer, are captured and concentrated using the current device design and the described experimental conditions. COMSOL (finite element multiphysics modeling software) calculations allow for directed device design development by exploring alternative device design parameters not yet tested experimentally. Modeling with COSMOL confirmed that for the current DC-iGDEP device design, Aβ monomer should not be captured for any reasonable experimental conditions. Details of the models used to evaluate the particle capture potential of the device can be found in Example 2. Modeling also predicts that by reducing the smallest sawtooth gap distance from 27 μm in the current design to ~10 nm, the increased field gradient strength required to allow monomer capture along with all intermediate species could be generated. By modeling the amyloid aggregates, oligomers, and monomers based on their unique electrophoretic and dielectrophoretic properties, the speed of the device design evolution can be accelerated while also being tailored for capturing particular bioanalytes and positioning them along the length of the channel.

In conclusion, this study demonstrates that DC-iGDEP can be used to manipulate and selectively capture Aβ amyloid fibrils, while influencing but not capturing Aβ monomer. DC-iGDEP successfully combines high enrichment of fibrils (up to 520%) with short analysis times (1-15 min) on a cost effective platform. Production and operation of the DC-iGDEP microdevices using PDMS are very simple. This initial study and related simulations indicate that this technique has the potential to rapidly isolate and concentrate various Aβ aggregate structures intermediate between monomer and mature fibrils. Development of new rapid and gentle separation techniques for isolating and characterizing amyloid aggregates is essential for understanding the role of protein aggregation in amyloid-linked diseases.

Example 2

A) Details of DC-iGDEP Device Fabrication

The DC-iGDEP devices were fabricated utilizing standard photolithography, fabrication, and bonding techniques. (C. Mack, Fundamental Principles of Optical Lithography: The Science of Microfabrication, Wiley, Hoboken, 2008.) Photomasks were designed in AutoCAD (Autodesk; San Rafael, Calif., USA), and photolithographic positive stamps were made using AZ P4620 photoresist (AZ Electronic Materials; Branchburg, N.J., USA) and contrast enhancement material CEM388SS (Shin-Etsu MicroSi; Phoenix, Ariz., USA). Device channels were fabricated from polydimethylsiloxane (PDMS) with a microscope slide coverplate. The PDMS channels were cast using Sylgard 184 silicone elastomer kit PDMS (Dow/Corning; Midland, Mich., USA). Shortly after the PDMS portion of the device was fabricated, access holes were made using a hole punch (3 mm diameter through 0.5-1 cm of PDMS), and then the PDMS portion of the device was sealed to the glass cover plate by plasma oxidation followed by contact sealing. (K. Haubert, T. Drier and D. Beebe, Lab Chip, 2006, 6, 1548-1549.) The geometry of the separatory portion of the DC-iGDEP channel consisted of successive triangular units that extended into the open volume to induce local electric field gradients. The insulating PDMS 60° triangles began with a base length of 6 μm and a height of 5.2 μm. Their side length and width increased by 40 μm after every six repeats (FIG. 3), resulting in an initial gap distance of 945 μM and a final gap distance of 27 μm. The separatory portion of the DC-iGDEP channel connected the two reservoirs created by the hole punch, where sample and buffer were introduced into the channel. The channel depth ranged from 13 to 16 μm.

Sample was introduced via the reservoir at the end of the channel with the larger gap distance. After sample introduction, platinum wire electrodes (0.404 mm diameter, 99.9% purity; Alfa Aesar; Ward Hill, Mass., USA) were placed in each of the reservoirs in contact with the solution and attached to a power supply (Series 225, Bertram). The voltage was applied at a potential between 0 and 1000 V, for 1-15 min depending upon the experiment. Visualization was achieved using an Olympus inverted IX70 microscope with a mercury short arc H30 103 w/2 light source from OSRAM and an Olympus DAPI, FITC, Texas Red triple band pass cube (Olympus; Center Valley, Pa., USA).

Figure 7:
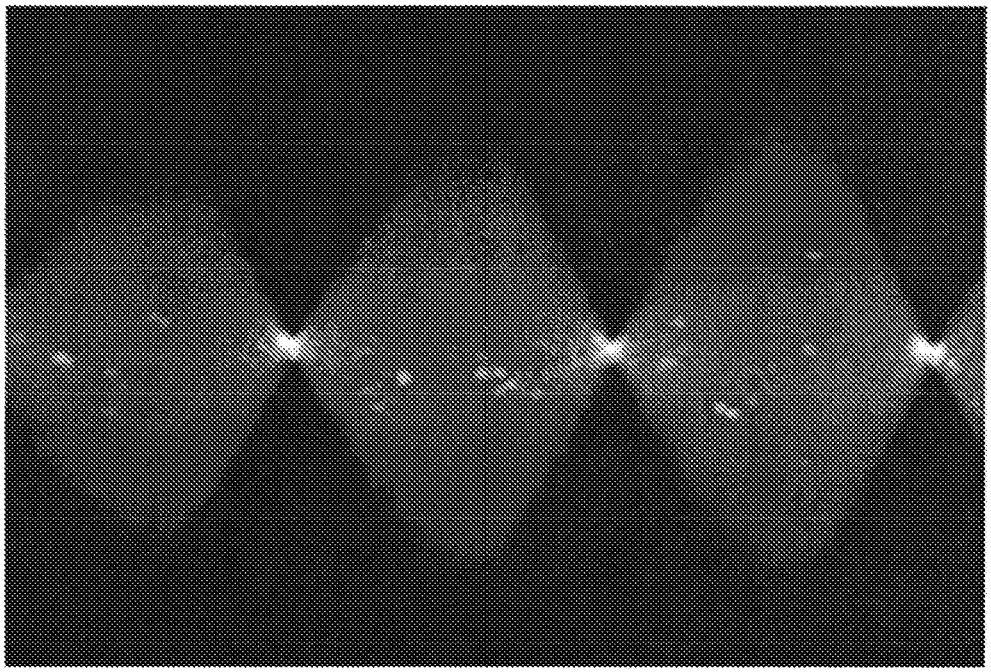
FIG. 7. Regions of interest (ROIs) indicated as described in the text. Three different areas were selected to determine the enrichment of fibril concentration in the capture zone using the fluorescence intensities in each region. The areas depicted here are larger than the actual ROIs used for ease of viewing.

Videos and still images were collected with a monochrome QICAM cooled CCD camera (Qlmaging, Inc.; Surrey, BC, Canada) and Streampix III image capture software (Norpix, Inc.; Montreal, QC, Canada). The fluorescence intensity was then analyzed with Image? (NIH; Bethesda, Md.). Three different regions of interest (ROI) were selected (FIG. 7). The ROIs represent the capture zone (gate), a background area within the channel (recess), and a background outside of the channel (PDMS). Table 2 uses the same ROIs described in FIG. 7. The data presented in Table 3 represent multiple replicates (n>3) with isolation events occurring in the same position. Ratios of the various ROIs were utilized to determine enrichment of fluorescent fibrils in the capture zone when compared to the rest of the microfluidic channel filled with sample as well as a background of the device outside of the channel. Each ROI represents equally sized areas.

TABLE 2

Fluorescence Intensity Values in ROIs for Fibril Samples.

| | Photo label | Intensity/Area | Ratio | |
|---|---|---|---|---|
| | | 400 V | | |
| Gate | 1 | 212.8 | | |
| Recess | 2 | 52.2 | Gate/Recess | 4.1 |
| PDMS | 3 | 35.9 | Gate/PDMS | 5.9 |
| | | 600 V | | |
| Gate | 1 | 207.0 | | |
| Recess | 2 | 40.0 | Gate/Recess | 5.2 |
| PDMS | 3 | 36.1 | Gate/PDMS | 5.7 |
| | | 800 V | | |
| Gate | 1 | 214.5 | | |
| Recess | 2 | 60.0 | Gate/Recess | 3.6 |
| PDMS | 3 | 36.1 | Gate/PDMS | 5.9 |
| | | 1000 V | | |
| Gate | 1 | 211.7 | | |
| Recess | 2 | 61.2 | Gate/Recess | 3.5 |
| PDMS | 3 | 36.1 | Gate/PDMS | 5.9 |

B) Preparation of Aβ (1-40) Monomers and Fibrils

Both Aβ (1-40) monomer and fibril samples were prepared as described in detail previously. (R. Picou, J. P. Moses, A. D. Wellman, I. Kheterpal and S. D. Gilman, Analyst, 2010, 135, 1631-1635; R. A. Picou, I. Kheterpal, A. D. Wellman, M. Minnamreddy, G. Ku and S. D. Gilman, J Chromatogr. B, 2011, 879, 627-632; B. O'Nuallain, A. K. Thakur, A. D. Williams, A. M. Bhattacharyya, S. Chen, G. Thiagarajan and R. Wetzel, in Methods Enzymol. 2006, 413, 34-74.) Briefly, Aβ (1-40) peptide (W. M Keck Foundation Biotechnology Research Laboratory, Yale University; New Haven, Conn.) and carboxyfluorescein (FAM) labeled Aβ (1-40) peptide (Anaspec Inc.; Fremont, Calif.) were first treated with trifluoroacetic acid (TFA) and hexafluoroisopropanol (HFIP) to remove any preexisting aggregates. For Aβ monomer samples, the solvent was evaporated off, and the peptides were dissolved in 10.00 mM Tris at pH 7.79. FAM-Aβ (1-40) monomer was mixed with Aβ (1-40) monomer at a mass ratio of 1:4. The total Aβ concentration of the monomer solution was determined to be 30 μM using a Shimadzu HPLC-UV instrument with detection at 215 nm as described previously. (R. Picou, J. P. Moses, A. D. Wellman, I. Kheterpal and S. D. Gilman, Analyst, 2010, 135, 1631-1635; R. A. Picou, I. Kheterpal, A. D. Wellman, M. Minnamreddy, G. Ku and S. D. Gilman, J Chromatogr. B, 2011, 879, 627-632; B. O'Nuallain, A. K. Thakur, A. D. Williams, A. M. Bhattacharyya, S. Chen, G. Thiagarajan and R. Wetzel, in Methods Enzymol. 2006, 413, 34-74.)

For the Aβ (1-40) fibril samples, TFA was evaporated off, and the peptides were dissolved in HFIP. The concentration of each peptide was determined using HPLC-UV. FAM-Aβ (1-40) monomer was mixed at a mass ratio of 1:4 with Aβ (1-40) monomer. HFIP was evaporated off, and the peptide mixture was dissolved stepwise in equal volumes of 2.0 mM NaOH and 2× phosphate buffered saline (PBS) containing 22.8 mM phosphate, 274 mM NaCl, 5.4 mM KCl and 0.1% NaN3 at pH 7.4. The samples were centrifuged at 50,000 g for a minimum of 10 hat 4° C. Fibril formation was initiated by addition of a small quantity (0.1% by weight of total Aβ monomer) of fibrillar aggregates to the supernatant from a previous fibril synthesis. The mixture was then incubated at 37° C. for 7 d. Depletion in monomer during fibril formation was monitored using HPLC-UV with detection at 215 nm as described previously. (R. Picou, J. P. Moses, A. D. Wellman, I. Kheterpal and S. D. Gilman, Analyst, 2010, 135, 1631-1635; R. A. Picou, I. Kheterpal, A. D. Wellman, M. Minnamreddy, G. Ku and S. D. Gilman, J Chromatogr. B, 2011, 879, 627-632; B. O'Nuallain, A. K. Thakur, A. D. Williams, A. M. Bhattacharyya, S. Chen, G. Thiagarajan and R. Wetzel, in Methods Enzymol. 2006, 413, 34-74.) Fibril growth was monitored using ThT fluorescence until complete (5-7 days), and the quality of fibrils was assessed by electron microscopy. For direct comparison with Aβ (1-40) monomer samples in DC-iGDEP analysis, fibril samples were buffer exchanged from PBS to 10.00 mM Tris electrophoresis buffer at pH 7.79. (I. Kheterpal, S. Zhou, K. D. Cook and R. Wetzel, Proc. Natl. Acad. Sci. USA, 2000, 97, 13597-13601.) The monomer-equivalent concentrations of all samples were determined to be 30 μM by HPLC-UV.

C) COMSOL Mathematical Modeling

In order to aid in understanding and interpreting particle behavior within the sawtooth-patterned microchannel, the electric field distribution within the microdevice was determined numerically and plotted. This was accomplished using finite element analysis software COMSOL Multiphysics 4.1 (COMSOL, Inc., Burlington, Mass.) in the "conductive media DC" mode. Models created in this mode are time-independent calculations of field strength within an aqueous medium. COMSOL computes the electric field by solving the Laplace equation, $\nabla^2(\varphi)=0$, for potential distribution at various points throughout the channel, along a predefined mesh. The boundary conditions are defined as distinct potentials at the channel inlet and outlet and electrical insulators at the channel walls.

A properly scaled model of the main channel geometry was produced and imported into the COMSOL environment. In order to simplify the model, a 2D approximation of the channel was utilized. Due to the placement of electrodes in distant reservoirs and the high width to depth ratio of the channel, the effects of channel depth on electrical potential were neglected. The effects of particles on the electric field distribution were also neglected.

Reservoir-channel junctions were set to predetermined potentials similar to those used during experiments. $V_{inlet}$ and $V_{outlet}$ were 0 V and −550 V, respectively. All other boundaries (representing PDMS and glass walls) were set to be perfect insulators; an approximation justified by the large difference in conductivity between the fluid medium and the channel walls. The conductivity and relative permittivity of the medium were set at 1.2 S/m and 78, respectively. This conductivity is consistent with values that can be obtained using standard phosphate-buffered saline.

A triangular mesh was applied to the entire channel area. The mesh contained approximately 97,000 triangular elements and 680 vertex elements. Through finite element analysis, the software approximates the electric potential at each mesh point. From these numerical values other useful parameters relevant to electrokinesis and dielectrophoresis may be determined, such as electric field strength, $|E|$, and the gradient of square of the electric field, $\nabla|E|^2$. Built-in tools enable graphic representation of the resulting data.

Figure 8:
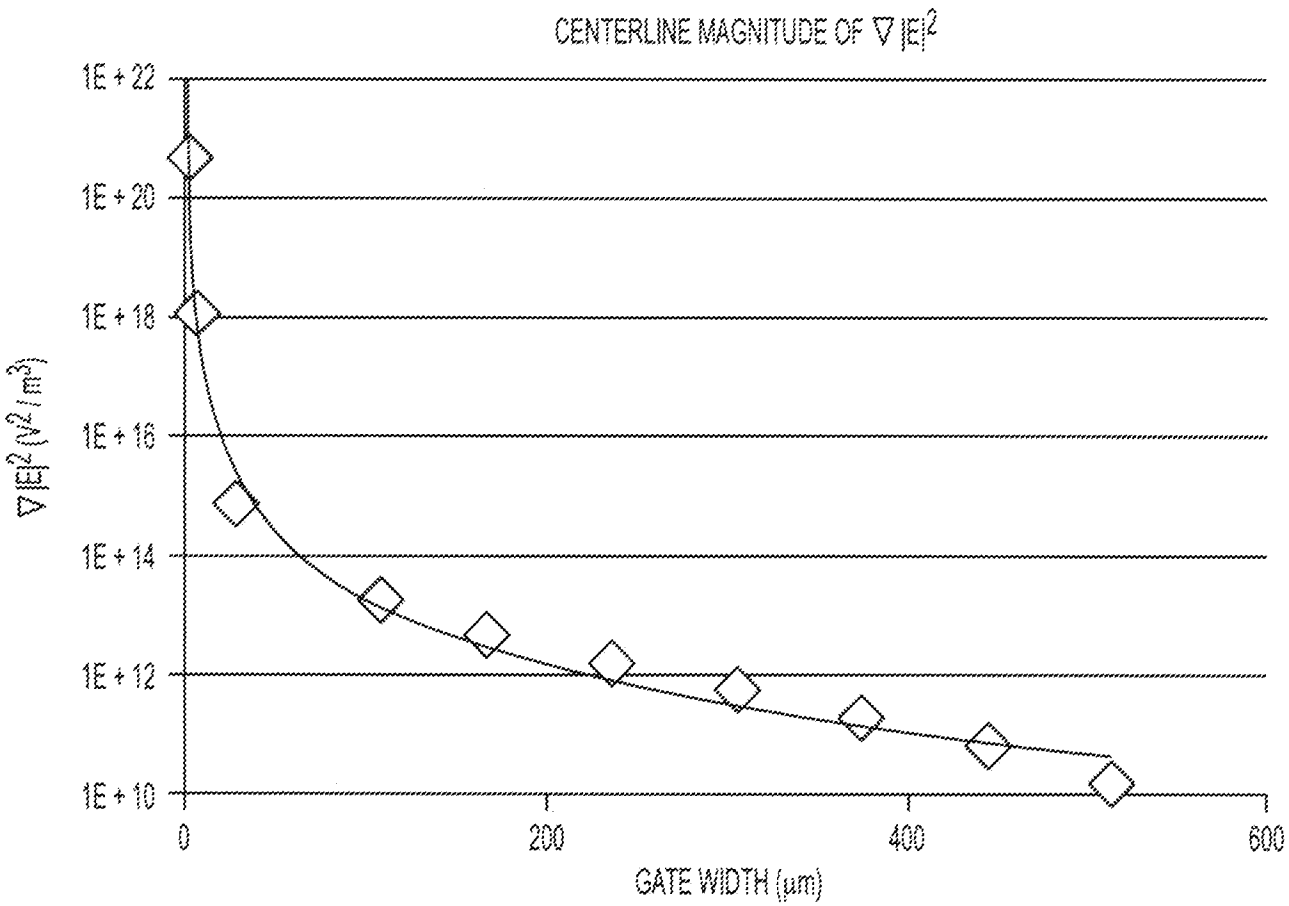
FIG. 8. Plot showing computed magnitudes of $\nabla|E|^2$ along the microchannel centerline versus gate width. Vertical axis is plotted using a logarithmic scale. The trend line shows that the relationship between data points can be approximated using a power function.

Since dielectrophoretic force is proportional to $\nabla|E|^2$, the magnitude of this term along the channel centerline was extracted from the COMSOL model using a 2D cut line. Localized maxima from this dataset correspond to channel constrictions or gates along the sawtooth pattern. When these values of $\nabla|E|^2$ are plotted as a function of gate width, the relationship can be reasonably approximated with a power function (FIG. 8). Visualizing the data in this manner illustrates the rapid scaling of dielectrophoretic force with increasing geometric constriction of the channel.

Amongst other things, dielectrophoretic force is proportional to particle size. Thus, capture of smaller particles such as protein monomers will require larger values of $\nabla|E|^2$. FIG. 8 illustrates that drastically larger values of $\nabla|E|^2$ are attainable by increasing the constriction ratio at gates. Using the following assumptions and the $\nabla|E|^2$ values determined in FIG. 8, it was found that a gate width of ~10 nm would be sufficient to capture Aβ monomers. The assumptions used in the calculation were that there was negligible electroosmotic flow, the Aβ monomer is spherical with a diameter of ~2.5 nm, the monomer μEP is $1.2\times10^{-4}$ $cm^2/(Vs)$, the viscosity and permittivity of the medium are similar to that of water, and the conductivity of the Aβ monomer is significantly less than that of the fluid medium.

Although the foregoing specification fully discloses and enables the present invention, it is not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

SEQUENCE LISTING

<160> NUMBER OF SEQ ID NOS: 79

<210> SEQ ID NO 1
<211> LENGTH: 292
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (2)..(2)
<223> OTHER INFORMATION: Any amino acid

<400> SEQUENCE: 1

Glu Xaa Pro Ile Ala Tyr Gly Ser Arg Trp Ile Val Ile Thr Arg Gly
1 5 10 15

Pro Ala Gly His Gly Pro Gly Thr Ala Ala Gly Val Gly Gly Gly Leu
20 25 30

Val Gln Pro Gly Gly Ser Leu Arg Leu Ser Cys Ala Ala Ser Gly Phe
35 40 45

Thr Phe Ser Ser Tyr Ala Met Ser Trp Val Arg Gln Ala Pro Gly Lys
50 55 60

Gly Leu Glu Trp Val Ser Ala Ile Ser Gly Ser Gly Gly Ser Thr Tyr
65 70 75 80

Tyr Ala Asp Ser Val Lys Gly Arg Phe Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Lys Ser Tyr Gly Ser Val Lys Ile Ser Cys
115 120 125

Phe Asp Tyr Trp Gly Gln Ser Thr Leu Val Thr Val Ser Ser Gly Gly
130 135 140

Gly Gly Ser Gly Gly Gly Gly Ser Gly Gly Gly Gly Ser Glu Ile Val
145 150 155 160

Leu Thr Gln Ser Pro Asp Ser Leu Ala Val Ser Leu Gly Glu Arg Ala
165 170 175

Thr Ile Asn Cys Lys Ser Ser Gln Ser Val Leu Tyr Asn Ser Asn Asn
180 185 190

Lys Asn Tyr Leu Ala Trp Tyr Gln Gln Lys Pro Gly Gln Ser Pro Glu
195 200 205

Leu Leu Ile Tyr Trp Ala Ser Thr Arg Glu Ser Gly Val Pro Asp Arg
210 215 220

Phe Ser Gly Ser Gly Ser Gly Thr Glu Phe Thr Leu Thr Ile Ser Ser
225 230 235 240

Leu Gln Ala Glu Asp Val Ala Val Tyr Tyr Cys Gln Gln Phe Tyr Ser
245 250 255

Thr Pro Pro Thr Phe Gly Gln Gly Thr Lys Leu Glu Ile Lys Arg Ala
260 265 270

Ala Ala His His His His His His Gly Ala Ala Glu Gln Lys Leu Ile
275 280 285

Ser Glu Glu Asp
290

<210> SEQ ID NO 2
<211> LENGTH: 268
<212> TYPE: PRT
<213> ORGANISM: Artificial Sequence <220> FEATURE:
<223> OTHER INFORMATION: Description of Artificial Sequence: Synthetic
polypeptide

<400> SEQUENCE: 2

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Ser
20 25 30

Ser Tyr Pro Met Ser Trp Val Arg Gln Ala Pro Gly Lys Gly Leu Glu
35 40 45

Trp Val Ser Ala Ile Gln His Thr Gly Ala Pro Thr Thr Tyr Ala Asp
50 55 60

Ser Val Lys Gly Arg Phe Thr Ile Ser Arg Asp Asn Ser Lys Asn Thr
65 70 75 80

Leu Tyr Leu Gln Met Asn Ser Leu Arg Ala Glu Asp Thr Ala Val Tyr
85 90 95

Tyr Cys Ala Lys Ala Phe Pro Pro Phe Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Thr Asp Ile Gln Met Thr Gln Ser Pro Ser Ser
130 135 140

Leu Ser Ala Ser Val Gly Asp Arg Val Thr Ile Thr Cys Arg Ala Ser
145 150 155 160

Gln Ser Ile Ser Ser Tyr Leu Asn Trp Tyr Gln Gln Lys Pro Gly Lys
165 170 175

Ala Pro Lys Leu Leu Ile Tyr Ser Ala Ser Ser Leu Gln Ser Gly Val
180 185 190

Pro Ser Arg Phe Ser Gly Ser Gly Ser Gly Thr Asp Phe Thr Leu Thr
195 200 205

Ile Ser Ser Leu Gln Pro Glu Asp Phe Ala Thr Tyr Tyr Cys Gln Gln
210 215 220

Arg Glu Thr Gly Pro Lys Ala Phe Gly Gln Gly Thr Lys Val Glu Ile
225 230 235 240

Lys Arg Ala Ala Ala His His His His His His Gly Ala Ala Glu Gln
245 250 255

Lys Leu Ile Ser Glu Glu Asp Leu Asn Gly Ala Ala
260 265

<210> SEQ ID NO 3
<211> LENGTH: 268
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Met Ala Glu Val Gln Leu Leu Glu Ser Gly Gly Gly Leu Val Gln Pro
1 5 10 15

Gly Gly Ser Leu Arg Leu Ser Cys Ala Ala Ser Gly Phe Thr Phe Ser
20 25 30

Ser Tyr Ala Met Ser Trp Val Arg Gln Ala Pro Gly Lys Gly Leu Glu
35 40 45

Trp Val Ser Ser Ile Gln Pro Glu Gly Arg Arg Thr Ala Tyr Val Asp
50 55 60

```
Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Pro Pro Glu Arg Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Tyr Ser Thr Pro Asn Thr Phe Gly Gln Gly Thr Lys Val Glu Ile
225                 230                 235                 240

Lys Arg Ala Ala Ala His His His His His His Gly Ala Ala Glu Gln
                245                 250                 255

Lys Leu Ile Ser Glu Glu Asp Leu Asn Gly Ala Ala
            260                 265


<210> SEQ ID NO 4
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Gly Gln Lys Gly Gly Gly Thr Gln Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys His Phe Glu Asn Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
```

```
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser His Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Thr Arg Arg Pro Pro Ser Thr Phe Gly Gln Gly Thr Lys Val Glu Ile
225                 230                 235                 240

Lys Arg Ala Ala Ala His His His His His His Gly Ala Ala Glu Gln
                245                 250                 255

Lys Leu Ile Ser Glu Glu Asp Leu Asn Gly Ala Ala
            260                 265


<210> SEQ ID NO 5
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asn Ile Ser Ser Ala Gly Lys Gly Leu Glu Trp Val Ser
    50                  55                  60

Ser Ile Asp Asp Ser Gly Ala Ser Thr Tyr Tyr Ala Asp Ser Val Lys
65                  70                  75                  80

Gly Arg Phe Thr Ile Ser Arg Asp Asn Ser Lys Asn Thr Leu Tyr Leu
                85                  90                  95

Gln Met Asn Ser Leu Arg Ala Glu Asp Thr Ala Val Tyr Tyr Cys Ala
            100                 105                 110

Lys Asp Ser Ala Ser Phe Asp Tyr Trp Gly Gln Gly Thr Leu Val Thr
        115                 120                 125

Val Ser Ser Gly Gly Gly Gly Ser Gly Gly Gly Gly Ser Gly Gly Gly
    130                 135                 140

Gly Ser Thr Asp Ile Gln Met Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Thr Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
    210                 215                 220

Leu Gln Pro Glu Asp Phe Ala Thr Tyr Tyr Cys Gln Gln Ser Ala Ala
225                 230                 235                 240
```

```
Ser Pro Ser Thr Phe Gly Gln Gly Thr Lys Val Glu Ile Lys Arg Ala
                245                 250                 255

Ala Ala His His His His His His Gly Ala Ala Glu Gln Lys Leu Ile
            260                 265                 270

Ser Glu Glu Asp Leu Asn Gly Ala Ala
        275                 280


<210> SEQ ID NO 6
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Tyr Ile Ala Ser Gly Gly Asp Thr Thr Asn Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Ala Ser Ala Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Tyr Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Ser Asn Asp Pro Tyr Thr Phe Gly Gln Gly Thr Lys Val Glu Ile
225                 230                 235                 240

Lys Arg Ala Ala Ala His His His His His His Gly Ala Ala Glu Gln
                245                 250                 255

Lys Leu Ile Ser Glu Glu Asp Leu Asn Gly Ala Ala
            260                 265


<210> SEQ ID NO 7
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 7

Met Ala Glu Val Gln Leu Val Glu Ser Gly Gly Gly Val Val Gln Pro
1 5 10 15

Gly Arg Ser Leu Arg Leu Ser Cys Ala Ala Ser Gly Phe Thr Phe Ser
20 25 30

Ser Tyr Gly Met His Trp Val Arg Gln Ala Pro Gly Lys Gly Leu Glu
35 40 45

Trp Val Ala Val Ile Ser Tyr Asp Gly Ser Asn Lys Tyr Tyr Ala Asp
50 55 60

Ser Val Lys Gly Arg Phe Thr Ile Ser Arg Asp Asn Ser Lys Asn Thr
65 70 75 80

Leu Tyr Leu Gln Val Asn Ser Leu Arg Ala Glu Asp Thr Ala Val Tyr
85 90 95

Tyr Cys Ala Arg Ile Asn Ala Lys Trp Gly Gln Gly Thr Leu Val Thr
100 105 110

Val Ser Ser Gly Gly Gly Gly Ser Gly Gly Gly Gly Ser Gly Gly Ser
115 120 125

Ala Leu Asp Ile Gln Met Thr Gln Ser Pro Ser Ser Leu Ser Ala Ser
130 135 140

Val Gly Asp Arg Val Thr Ile Thr Cys Arg Ala Ser Gln Ser Ile Ser
145 150 155 160

Ser Tyr Leu Asn Trp Tyr Gln Gln Lys Pro Gly Lys Ala Pro Lys Leu
165 170 175

Leu Ile Tyr Ala Ala Ser Ser Leu Gln Ser Gly Val Pro Ser Arg Phe
180 185 190

Ser Gly Ser Gly Ser Gly Thr Asp Phe Thr Leu Thr Ile Ser Ser Leu
195 200 205

Gln Pro Gly Asp Phe Ala Thr Tyr Tyr Cys Gln Gln Ser Tyr Ser Thr
210 215 220

Pro Thr Phe Gly Gln Gly Thr Lys Val Glu Ile Lys Arg Ala Ala Ala
225 230 235 240

His His His His His His Gly Ala Ala Glu Gln Lys Leu Ile Ser Glu
245 250 255

Glu Asp Leu Asn Gly Ala Ala
260

<210> SEQ ID NO 8
<211> LENGTH: 877
<212> TYPE: DNA
<213> ORGANISM: Artificial sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (715)..(718)
<223> OTHER INFORMATION: a, c, t, g, unknown or other
<220> FEATURE:
<221> NAME/KEY: misc_feature
<222> LOCATION: (725)..(725)
<223> OTHER INFORMATION: a, c, t, g, unknown or other
<220> FEATURE:
<221> NAME/KEY: misc_feature
<222> LOCATION: (729)..(729)
<223> OTHER INFORMATION: a, c, t, g, unknown or other
<220> FEATURE:
<221> NAME/KEY: misc_feature
<222> LOCATION: (733)..(733)
<223> OTHER INFORMATION: a, c, t, g, unknown or other
<220> FEATURE:

<221> NAME/KEY: misc_feature
<222> LOCATION: (737)..(737)
<223> OTHER INFORMATION: a, c, t, g, unknown or other
<220> FEATURE:
<221> NAME/KEY: misc_feature
<222> LOCATION: (789)..(789)
<223> OTHER INFORMATION: a, c, t, g, unknown or other
<220> FEATURE:
<221> NAME/KEY: misc_feature
<222> LOCATION: (807)..(807)
<223> OTHER INFORMATION: a, c, t, g, unknown or other
<220> FEATURE:
<221> NAME/KEY: misc_feature
<222> LOCATION: (810)..(810)
<223> OTHER INFORMATION: a, c, t, g, unknown or other
<220> FEATURE:
<221> NAME/KEY: misc_feature
<222> LOCATION: (833)..(833)
<223> OTHER INFORMATION: a, c, t, g, unknown or other
<220> FEATURE:
<221> NAME/KEY: misc_feature
<222> LOCATION: (844)..(844)
<223> OTHER INFORMATION: a, c, t, g, unknown or other
<220> FEATURE:
<221> NAME/KEY: misc_feature
<222> LOCATION: (852)..(852)
<223> OTHER INFORMATION: a, c, t, g, unknown or other
<220> FEATURE:
<221> NAME/KEY: misc_feature
<222> LOCATION: (858)..(859)
<223> OTHER INFORMATION: a, c, t, g, unknown or other
<220> FEATURE:
<221> NAME/KEY: misc_feature
<222> LOCATION: (865)..(867)
<223> OTHER INFORMATION: a, c, t, g, unknown or other

<400> SEQUENCE: 8 ttgttattac tcgcggccca gccggccatg gccgaggtgc agctgttgga gtctggggga 60 ggcttggtac agcctggggg gtccctgaga ctctcctgtg cagcctctgg attcaccttt 120 agcagctatc ccatgagctg ggtccgccag gctccaggga aggggctgga gtgggtctca 180 gcgattcagc atactggtgc gccgacaact tacgcagact ccgtgaaggg ccggttcacc 240 atctccagag acaattccaa gaacacgctg tatctgcaaa tgaacagcct gagagccgag 300 gacacggccg tatattactg tgcgaaagcg tttccgccgt ttgactactg gggccaggga 360 accctggtca ccgtctcgag cggtggaggc ggttcaggcg gaggtggcag cggcggtggc 420 gggtcgacgg acatccagat gacccagtct ccatcctccc tgtctgcatc tgtaggagac 480 agagtcacca tcacttgccg ggcaagtcag agcattagca gctatttaaa ttggtatcag 540 cagaaaccag ggaaagcccc taagctcctg atctattctg catcctcttt gcaaagtggg 600 gtcccatcaa ggttcagtgg cagtggatct gggacagatt tcactctcac catcagcagt 660 ctgcaacctg aagattttgc aacttactac tgtcaacagc gggagactgg gcctnnnngt 720 tcggncaang gancaangtg gaaatcaaac gggcggccgc acatcatcat caccatcacg 780 gggccgcana acaaaaactc atctcanaan aggatctgaa tggggccgca tanactgttg 840 aaanttgttt ancaaacnnc atacnnnaaa ttcattt 877

<210> SEQ ID NO 9
<211> LENGTH: 877
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (807)..(807)

<223> OTHER INFORMATION: a, c, t, g, unknown or other
<220> FEATURE:
<221> NAME/KEY: misc_feature
<222> LOCATION: (810)..(810)
<223> OTHER INFORMATION: a, c, t, g, unknown or other
<220> FEATURE:
<221> NAME/KEY: misc_feature
<222> LOCATION: (852)..(852)
<223> OTHER INFORMATION: a, c, t, g, unknown or other

<400> SEQUENCE: 9 ttgttattac tcgcggccca gccggcctgg ccgaggtgca gctgttggag tctgggggag 60 gcttggtaca gcctgggggg tccctgagac tctcctgtgc agcctctgga ttcaccttta 120 gcagctatgc catgagctgg gtccgccagg ctccagggaa ggggctggag tgggtctcat 180 ctattcagcc tgagggtagg cggacagcgt acgtagactc cgtgaagggc cggttcacca 240 tctccagaga caattccaag aacacgctgt atctacaaat gaacagcctg agagccgagg 300 acacggccgt atattactgt gcgaaaccgc cggagaggtt tgactactgg ggccagggaa 360 ccctggtcac cgtctcgagc ggtggaggcg gttcaggcgg aggtggcagc ggcggtggcg 420 ggtcgacgga catccagatg acccagtctc catcctccct gtctgcatct gtaggagaca 480 gagtcaccat cacttgccgg gcaagtcaga gcattagcag ctatttaaat tggtatcagc 540 agaaaccagg gaaagcccct aagctcctga tctatgctgc atccagtttg caaagtgggg 600 tcccatcaag gttcagtggc agtggatctg ggacagattt cactctcacc atcagcagtc 660 tgcaacctga agattttgca acttactact gtcaacagag ttacagtacc cctaatacgt 720 tcggccaagg gaccaaggtg gaaatcaaac gggcggccgc acatcatcat caccatcacg 780 gggccgcaga acaaaaactc atctcanaan aggatctgaa tggggccgca tagactgttg 840 aaagttgttt ancaaacctc atacagaaaa ttcattt 877

<210> SEQ ID NO 10
<211> LENGTH: 821
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10 ccatggccca ggtacagctg caggagtcgg gggaggcttg gtacagcctg gggggtccct 60 gagactctcc tgtgcagcct ctggattcac ctttagcagc tatgccatga gctgggtccg 120 ccaggctcca gggaaggggc tggagtgggt ctcagctatt agtggtagtg gtggtagcac 180 atactacgca gactccgtga agggccgatt caccatctcc agagacaatt ccaagaacac 240 gctgtatctg caaatgaaca gcctgagagc tgaggacacg gctgtgtatt actgtgcgaa 300 gagctatggt tcagttaaaa taagctgctt tgactactgg ggccagagca ccctggtcac 360 cgtctcctca ggtggaggcg gttcaggcgg aggtggctct ggcggtggcg gatcggaaat 420 tgtgctgacg cagtctccag actccctggc tgtgtctctg ggcgagaggg ccaccatcaa 480 ctgcaagtcc agccagagtg ttctttacaa ctccaacaat aagaactact tagcttggta 540 ccagcagaaa ccaggacagt ctcctgagtt gctcatttac tgggcatcaa cccgggaatc 600 cggggtccct gaccgattca gtggcagcgg gtctgggaca gaattcactc ttaccatcag 660 cagcctgcag gctgaggatg tggcagttta ttactgtcag caattttata gtactcctcc 720 gacttttggc caggggacca agctggagat caaacgtgcg gccgcacatc atcatcacca 780 tcacggggcc gcagaacaaa aactcatctc agaagaggat c 821

<210> SEQ ID NO 11
<211> LENGTH: 822
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11 ccatggccga ggtgcagctg ttggagtctg ggggaggctt ggtacagcct ggggggtccc 60 tgagactctc ctgtgcagcc tctggattca cctttagcag ctatgccatg agctgggtcc 120 gccaggctcc agggaagggg ctggagtggg tctcatcgat tggtcagaag ggtggtggta 180 cacagtacgc agactccgtg aagggccggt tcaccatctc cagagacaat tccaagaaca 240 cgctgtatct gcaaatgaac agcctgagag ccgaggacac ggccgtatat tactgtgcga 300 aacattttga gaattttgac tactggggcc agggaaccct ggtcaccgtc tcgagcggtg 360 gaggcggttc aggcggaggt ggcagcggcg gtggcgggtc gacggacatc cagatgaccc 420 agtctccatc ctccctgtct gcatctgtag gagacagagt caccatcact tgccgggcaa 480 gtcagagcat tagcagctat ttaaattggt atcagcagaa accagggaaa gcccctaagc 540 tcctgatcta tgctgcatcc catttgcaaa gtggggtccc atcaaggttc agtggcagtg 600 gatctgggac agatttcact ctcaccatca gcagtctgca acctgaagat tttgcaactt 660 actactgtca acagacgcgt aggccgcctt ctacgttcgg ccaagggacc aaggtggaaa 720 tcaaacgggc ggccgcacat catcatcacc atcacggggc cgcagaacaa aaactcatct 780 cagaagagaa tcactagtgc ggccgcctgc aggtcgacca ta 822

<210> SEQ ID NO 12
<211> LENGTH: 843
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (816)..(816)
<223> OTHER INFORMATION: a, c, t, g, unknown or other
<220> FEATURE:
<221> NAME/KEY: misc_feature
<222> LOCATION: (826)..(826)
<223> OTHER INFORMATION: a, c, t, g, unknown or other
<220> FEATURE:
<221> NAME/KEY: misc_feature
<222> LOCATION: (832)..(833)
<223> OTHER INFORMATION: a, c, t, g, unknown or other
<220> FEATURE:
<221> NAME/KEY: misc_feature
<222> LOCATION: (836)..(836)
<223> OTHER INFORMATION: a, c, t, g, unknown or other
<220> FEATURE:
<221> NAME/KEY: misc_feature
<222> LOCATION: (840)..(840)
<223> OTHER INFORMATION: a, c, t, g, unknown or other

<400> SEQUENCE: 12 ccatggccga ggtgcagctg ttggagtctg ggggaggctt ggtacagcct ggggggtccc 60 tgagactctc ctgtgcagcc tctggattca cctttagcag ctatgccatg agctgggtcc 120 gccaggctcc agggaagggg ctggagtggg tctcaaatat tagtagtgca gggaaggggc 180 tggagtgggt ctcaagtatt gatgattctg gtgcttctac atattacgca gactccgtga 240 agggccggtt caccatctcc agagacaatt ccaagaacac gctgtatctg caaatgaaca 300 gcctgagagc cgaggacacg gccgtatatt actgtgcgaa agattctgct tcttttgact 360 actggggcca gggaaccctg gtcaccgtct cgagcggtgg aggcggttca ggcggaggtg 420 gcagcggcgg tggcgggtcg acggacatcc agatgaccca gtctccatcc tccctgtctg 480 catctgtagg agacagagtc accatcactt gccgggcaag tcagagcatt agcagctatt 540 taaattggta tcagcagaaa ccagggaaag cccctaagct cctgatctat actgcatcca 600 gtttgcaaag tggggtccca tcaaggttca gtggcagtgg atctgggaca gatttcactc 660 tcaccatcag cagtctgcaa cctgaagatt ttgcaactta ctactgtcaa cagtctgctg 720 ctagtccttc tacgttcggc caagggacca aggtggaaat caaacgggcg gccgcacatc 780 accatcacca tcacggggcc gcagaacaaa aactcntctc agaagnggat cnnaangggn 840 ccg 843

<210> SEQ ID NO 13
<211> LENGTH: 879
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (784)..(784)
<223> OTHER INFORMATION: a, c, t, g, unknown or other
<220> FEATURE:
<221> NAME/KEY: misc_feature
<222> LOCATION: (788)..(789)
<223> OTHER INFORMATION: a, c, t, g, unknown or other
<220> FEATURE:
<221> NAME/KEY: misc_feature
<222> LOCATION: (791)..(791)
<223> OTHER INFORMATION: a, c, t, g, unknown or other
<220> FEATURE:
<221> NAME/KEY: misc_feature
<222> LOCATION: (811)..(815)
<223> OTHER INFORMATION: a, c, t, g, unknown or other
<220> FEATURE:
<221> NAME/KEY: misc_feature
<222> LOCATION: (830)..(830)
<223> OTHER INFORMATION: a, c, t, g, unknown or other
<220> FEATURE:
<221> NAME/KEY: misc_feature
<222> LOCATION: (835)..(835)
<223> OTHER INFORMATION: a, c, t, g, unknown or other
<220> FEATURE:
<221> NAME/KEY: misc_feature
<222> LOCATION: (853)..(854)
<223> OTHER INFORMATION: a, c, t, g, unknown or other
<220> FEATURE:
<221> NAME/KEY: misc_feature
<222> LOCATION: (862)..(863)
<223> OTHER INFORMATION: a, c, t, g, unknown or other
<220> FEATURE:
<221> NAME/KEY: misc_feature
<222> LOCATION: (867)..(867)
<223> OTHER INFORMATION: a, c, t, g, unknown or other
<220> FEATURE:
<221> NAME/KEY: misc_feature
<222> LOCATION: (872)..(872)
<223> OTHER INFORMATION: a, c, t, g, unknown or other
<220> FEATURE:
<221> NAME/KEY: misc_feature
<222> LOCATION: (875)..(876)
<223> OTHER INFORMATION: a, c, t, g, unknown or other

<400> SEQUENCE: 13 ttgttattac tcgcggccca gccggccatg gccgaggtgc agctgttgga gtctggggga 60

```
ggcttggtac agcctggggg gtccctgaga ctctcctgtg cagcctctgg attcaccttt    120

agcagctatg ccatgagctg ggtccgccag gctccaggga aggggctgga gtgggtctca    180

tatattgcta gtggtggtga tactacaaat tacgcagact ccgtgaaggg ccggttcacc    240

atctccagag acaattccaa gaacacgctg tatctgcaaa tgaacagcct gagagccgag    300

gacacggccg tatattactg tgcgaaaggt gcttctgctt ttgactactg gggccaggga    360

accctggtca ccgtctcgag cggtggaggc ggttcaggcg gaggtggcag cggcggtggc    420

gggtcgacgg acatccagat gacccagtct ccatcctccc tgtctgcatc tgtaggagac    480

agagtcacca tcacttgccg ggcaagtcag agcattagca gctatttaaa ttggtatcag    540

cagaaaccag ggaaagcccc taagctcctg atctatgctg catcctattt gcaaagtggg    600

gtcccatcaa ggttcagtgg cagtggatct gggacagatt tcactctcac catcagcagt    660

ctgcaacctg aagattttgc aacttactac tgtcaacaga gttctaatga tccttatacg    720

ttcggccaag ggaccaaggt ggaaatcaaa cgggcggccg cacatcatca tcaccatcac    780

gggngccnna naacaaaaac tcatctcaaa nnnnntctga atgggggccn catanactgt    840

tgaaagttgt ttnnaaacct cntacanaaa antcnnttt                           879
```

<210> SEQ ID NO 14
<211> LENGTH: 776
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
atggccgagg tgcagctggt ggagtctggg ggaggcgtgg tccagcctgg gaggtccctg     60

agactctcct gtgcagcctc tggattcacc ttcagtagct atggcatgca ctgggtccgc    120

caggccccag gcaaggggct ggagtgggtg gcagttatat catatgatgg aagtaataaa    180

tactatgcag actccgtgaa gggccgattc accatctcca gagacaattc caagaacacg    240

ctgtatctgc aagtgaacag cctgagagct gaggacacgg ccgtgtatta ctgtgcaaga    300

attaatgcga agtggggcca aggtaccctg gtcaccgtct cgagtggtgg aggcggttca    360

ggcggaggtg gctctggcgg tagtgcactt gacatccaga tgacccagtc tccatcctcc    420

ctgtctgcat ctgtaggaga cagagtcacc atcacttgcc gggcaagtca gagcattagc    480

agctatttaa attggtatca gcagaaacca gggaaagccc ctaagctcct gatctatgct    540

gcatccagtt tgcaaagtgg ggtcccatca aggttcagtg gcagtggatc tgggacagat    600

ttcactctca ccatcagcag tctgcaacct ggagattttg caacttacta ctgtcaacag    660

agttacagta ccccgacgtt cgggcaaggg accaaggtgg aaatcaaacg tgcggccgca    720

catcatcatc accatcacgg ggccgcagaa caaaaactca tctcagaaga ggatct        776
```

<210> SEQ ID NO 15
<211> LENGTH: 278
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

```
Met Ala Gln Val Gln Leu Gln Glu Ser Gly Gly Gly Leu Val Gln Pro
1               5                   10                  15
```

```
Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Ser Gly Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Tyr Gly Ser Val Lys Ile Ser Cys Phe Asp Tyr
            100                 105                 110

Trp Gly Gln Ser Thr Leu Val Thr Val Ser Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Asn Ser Asn Asn Lys Asn Tyr
                165                 170                 175

Leu Ala Trp Tyr Gln Gln Lys Pro Gly Gln Ser Pro Glu Leu Leu Ile
            180                 185                 190

Tyr Trp Ala Ser Thr Arg Glu Ser Gly Val Pro Asp Arg Phe Ser Gly
        195                 200                 205

Ser Gly Ser Gly Thr Glu Phe Thr Leu Thr Ile Ser Ser Leu Gln Ala
    210                 215                 220

Glu Asp Val Ala Val Tyr Tyr Cys Gln Gln Phe Tyr Ser Thr Pro Pro
225                 230                 235                 240

Thr Phe Gly Gln Gly Thr Lys Leu Glu Ile Lys Arg Ala Ala Ala His
                245                 250                 255

His His His His His Gly Ala Ala Glu Gln Lys Leu Ile Ser Glu Glu
            260                 265                 270

Asp Leu Asn Gly Ala Ala
        275


<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Ala Met Ser
1               5


<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ile Ser Gly Ser Gly Gly Ser Thr Tyr Tyr Ala Asp Ser Val Lys
1               5                   10                  15
```

Gly

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Ser Tyr Gly Ser Val Lys Ile Ser Cys Phe Asp Tyr
1 5 10

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Lys Ser Ser Gln Ser Val Leu Tyr Asn Ser Asn Asn Lys Asn Tyr Leu
1 5 10 15

Ala

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Trp Ala Ser Thr Arg Glu Ser
1 5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Gln Gln Phe Tyr Ser Thr Pro Pro Thr
1 5

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22 agctatgcca tgagc 15

<210> SEQ ID NO 23
<211> LENGTH: 51
<212> TYPE: DNA
<213> ORGANISM: Artificial Sequence <220> FEATURE:
<223> OTHER INFORMATION: Description of Artificial Sequence: Synthetic
oligonucleotide

<400> SEQUENCE: 23 gctattagtg gtagtggtgg tagcacatac tacgcagact ccgtgaaggg c 51

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24 agctatggtt cagttaaaat aagctgcttt gactac 36

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25 aagtccagcc agagtgttct ttacaactcc aacaataaga actacttagc t 51

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26 tgggcatcaa cccgggaatc c 21

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27 cagcaatttt atagtactcc tccgact 27

<210> SEQ ID NO 28
<211> LENGTH: 5
<212> TYPE: PRT
<213> ORGANISM: Artificial Sequence
<220> FEATURE:
<223> OTHER INFORMATION: Synthetic peptide

<400> SEQUENCE: 28

Ser Tyr Pro Met Ser
1 5

<210> SEQ ID NO 29
<211> LENGTH: 17
<212> TYPE: PRT
<213> ORGANISM: Artificial Sequence
<220> FEATURE:

<223> OTHER INFORMATION: Synthetic peptide

<400> SEQUENCE: 29

Ala Ile Gln His Thr Gly Ala Pro Thr Thr Tyr Ala Asp Val Ser Lys
1 5 10 15

Gly

<210> SEQ ID NO 30
<211> LENGTH: 7
<212> TYPE: PRT
<213> ORGANISM: Artificial Sequence
<220> FEATURE:
<223> OTHER INFORMATION: Synthetic peptide

<400> SEQUENCE: 30

Ala Phe Pro Pro Phe Asp Tyr
1 5

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide

<400> SEQUENCE: 31

Arg Ala Ser Gln Ser Ile Ser Ser Tyr Leu Asn
1 5 10

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Ser Ala Ser Ser Leu Gln Ser
1 5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Gln Gln Arg Glu Thr Gly Pro Ile Leu
1 5

<210> SEQ ID NO 34
<211> LENGTH: 17
<212> TYPE: PRT
<213> ORGANISM: Artificial Sequence
<220> FEATURE:
<223> OTHER INFORMATION: Synthetic peptide

<400> SEQUENCE: 34

Ser Ile Gln Pro Glu Gly Arg Arg Thr Ala Tyr Val Asp Ser Val Lys
1 5 10 15

Gly

<210> SEQ ID NO 35
<211> LENGTH: 7

<212> TYPE: PRT
<213> ORGANISM: Artificial Sequence
<220> FEATURE:
<223> OTHER INFORMATION: Synthetic peptide

<400> SEQUENCE: 35

Pro Pro Glu Arg Phe Asp Tyr
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Ala Ala Ser Ser Leu Gln Ser
1 5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Gln Gln Ser Tyr Ser Thr Pro Asn Thr
1 5

<210> SEQ ID NO 38
<211> LENGTH: 30
<212> TYPE: PRT
<213> ORGANISM: Artificial Sequence
<220> FEATURE:
<223> OTHER INFORMATION: Synthetic peptide

<400> SEQUENCE: 38

Asn Ile Ser Ser Ala Gly Lys Gly Leu Glu Trp Val Ser Ser Ile Asp
1 5 10 15

Asp Ser Gly Ala Ser Thr Tyr Tyr Ala Asp Ser Val Lys Gly
20 25 30

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Asp Ser Ala Ser Phe Asp Tyr
1 5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Thr Ala Ser Ser Leu Gln Ser
1 5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Gln Gln Ser Ala Ala Ser Pro Ser Thr
1 5

<210> SEQ ID NO 42
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 42 agctatccca tgagc 15

<210> SEQ ID NO 43
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 43 gcgattcagc atactggtgc gccgacaact tacgcagact ccgtgaaggg c 51

<210> SEQ ID NO 44
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 44 gcgtttccgc cgtttgacta c 21

<210> SEQ ID NO 45
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 45 cgggcaagtc agagcattag cagctattta aat 33

<210> SEQ ID NO 46
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 46 tctgcatcct ctttgcaaag t 21

<210> SEQ ID NO 47
<211> LENGTH: 26
<212> TYPE: DNA
<213> ORGANISM: Artificial Sequence
<220> FEATURE:
<223> OTHER INFORMATION: Synthetic polynucleotide <220> FEATURE:
<221> NAME/KEY: misc_feature
<222> LOCATION: (22)..(25)
<223> OTHER INFORMATION: a, c, t, g, unknown or other

<400> SEQUENCE: 47 caacagcggg agactgggcc tnnnng 26

<210> SEQ ID NO 48
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 48 tctattcagc ctgagggtag gcggacagcg tacgtagact ccgtgaaggg c 51

<210> SEQ ID NO 49
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 49 ccgccggaga ggtttgacta c 21

<210> SEQ ID NO 50
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 50 gctgcatcca gtttgcaaag t 21

<210> SEQ ID NO 51
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 51 caacagagtt acagtacccc taatacg 27

<210> SEQ ID NO 52
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 52 aatattagta gtgcagggaa ggggctggag tgggtctcaa gtattgatga ttctggtgct 60 tctacatatt acgcagactc cgtgaagggc 90

<210> SEQ ID NO 53
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 53 gattctgctt cttttgacta c 21

<210> SEQ ID NO 54
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 54 actgcatcca gtttgcaaag t 21

<210> SEQ ID NO 55
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 55 caacagtctg ctgctagtcc ttctacg 27

<210> SEQ ID NO 56
<211> LENGTH: 17
<212> TYPE: PRT
<213> ORGANISM: Artificial Sequence
<220> FEATURE:
<223> OTHER INFORMATION: Synthetic peptide

<400> SEQUENCE: 56

Ser Ile Gly Gln Lys Gly Gly Gly Thr Gln Tyr Ala Asp Ser Val Lys
1 5 10 15

Gly

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

His Phe Glu Asn Phe Asp Tyr
1 5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Ala Ala Ser His Leu Gln Ser
1 5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Gln Gln Thr Arg Arg Pro Pro Ser Thr
1 5

<210> SEQ ID NO 60
<211> LENGTH: 17
<212> TYPE: PRT
<213> ORGANISM: Artificial Sequence
<220> FEATURE:
<223> OTHER INFORMATION: Synthetic peptide

<400> SEQUENCE: 60

Tyr Ile Ala Ser Gly Gly Asp Thr Thr Asn Tyr Ala Asp Ser Val Lys
1 5 10 15

Gly

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Gly Ala Ser Ala Phe Asp Tyr
1 5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ala Ala Ser Tyr Leu Gln Ser
1 5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Gln Gln Ser Ser Asn Asp Pro Tyr Thr
1 5

<210> SEQ ID NO 64
<211> LENGTH: 5
<212> TYPE: PRT
<213> ORGANISM: Artificial Sequence
<220> FEATURE:
<223> OTHER INFORMATION: Synthetic peptide

<400> SEQUENCE: 64

Ser Tyr Gly Met His
1 5

<210> SEQ ID NO 65
<211> LENGTH: 17
<212> TYPE: PRT
<213> ORGANISM: Artificial Sequence
<220> FEATURE:
<223> OTHER INFORMATION: Synthetic peptide

<400> SEQUENCE: 65

Val Ile Ser Tyr Asp Gly Ser Asn Lys Tyr Tyr Ala Asp Ser Val Lys
1 5 10 15

Gly

<210> SEQ ID NO 66
<211> LENGTH: 4
<212> TYPE: PRT
<213> ORGANISM: Artificial Sequence
<220> FEATURE:
<223> OTHER INFORMATION: Synthetic peptide

<400> SEQUENCE: 66

Ile Asn Ala Lys
1

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Gln Gln Ser Tyr Ser Thr Pro
1 5

<210> SEQ ID NO 68
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 68 tcgattggtc agaagggtgg tggtacacag tacgcagact ccgtgaaggg c 51

<210> SEQ ID NO 69
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 69 cattttgaga attttgacta c 21

<210> SEQ ID NO 70
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 70 gctgcatccc atttgcaaag t 21

<210> SEQ ID NO 71
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 71 caacagacgc gtaggccgcc ttctacg 27

<210> SEQ ID NO 72
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 72 tatattgcta gtggtggtga tactacaaat tacgcagact ccgtgaaggg c 51

<210> SEQ ID NO 73
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 73 ggtgcttctg cttttgacta c 21

<210> SEQ ID NO 74
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 74 gctgcatcct atttgcaaag t 21

<210> SEQ ID NO 75
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 75 caacagagtt ctaatgatcc ttatacg 27

<210> SEQ ID NO 76
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 76 agctatggca tgcac 15

<210> SEQ ID NO 77
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 77 gttatatcat atgatggaag taataaatac tatgcagact ccgtgaaggg c 51

<210> SEQ ID NO 78
<211> LENGTH: 12
<212> TYPE: DNA
<213> ORGANISM: Artificial Sequence
<220> FEATURE:

-continued

```
<223> OTHER INFORMATION: Synthetic polynucleotide

<400> SEQUENCE: 78

attaatgcga ag                                                    12


<210> SEQ ID NO 79
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 79

caacagagtt acagtacccc gacg                                       24
```

What is claimed is:

1. A direct current insulating gradient dielectrophoresis (DC-iGDEP) device for separating a target protein species in a biological sample based on a chemical or physical parameter, the device comprising: a sawtooth microfluidic channel configured to separate a target protein species from a biological sample, the channel having an inlet port and an outlet port, the sawtooth microfluidic channel including a plurality of pairs of opposing teeth lining both sides of the microfluidic channel, wherein the teeth have a triangular, asymmetric, crescent, starred or rounded shape, each of the plurality of pairs of opposing teeth including a gap between each of the plurality of pairs of opposing teeth, each of the gaps associated with each of the pairs of opposing teeth decreasing from about [1 mm] *50 μm* to about [0.5 mm] *1 μm* along the sawtooth microfluidic channel.

2. The device of claim 1, wherein the teeth have a triangular shape.

3. The device of claim 2, wherein the teeth have an equilateral triangular shape having a base and a height.

4. The device of claim 3, wherein the smallest teeth have a base length of 2-10 μm and a height of 2-10 μm, and wherein after every 1-10 repeats successive teeth are 25-50 μm larger in their side length and width.

[5. The device of claim 1, wherein the spacing of the initial gaps has a distance of about 945 pm and the spacing of the final gaps has a distance of about 27 pm.]

6. The device of claim 1, wherein the [spacing of the initial gaps has a distance of] *gaps associated with each of the pairs of opposing teeth decrease from* about 50 [pm and the spacing of the final gaps has a distance of] *μm to* about 1 nm.

[7. The device of claim 1, wherein the spacing of the initial gaps has a distance of about 50 pm and the spacing of the final gaps has a distance of about 1 pm.]

8. The device of claim 1, wherein the microfluidic channel has a depth of about 10 to 20 μm.

9. A method of separating from a biological sample a target species based on a chemical or physical parameter comprising, (a) providing the device of claim 1, (b) loading a loading volume of the sample into the inlet port, (c) applying a field to the device to separate particles or molecules in the sample based on the chemical or physical parameter, and (d) recovering the target species.

10. The method of claim 9, wherein the chemical or physical parameter is charge, size, permittivity, deformation, or shape.

11. The method of claim 9, wherein the target species is an Aβ aggregate.

12. The method of claim 11, further comprising contacting the recovered Aβ aggregates with an antibody to confirm the size of the Aβ aggregate.

13. The method of claim 12, wherein the antibody is specific for oligomeric Aβ aggregates.

14. The method of claim 12, wherein the antibody is a nanobody, and the nanobody is a C6, A4, E1, D5, 10H, 6E, D10 or BSEC1 nanobody.

15. The method of claim 9, wherein the biological sample has a volume of less than 100 microliters.

16. The method of claim 9, wherein the biological sample is brain tissue, serum, cerebrospinal fluid (CSF), urine or saliva.

17. The method of claim 9, wherein the field is applied for a period of time that is less than 20 minutes.

18. The method of claim 9, wherein the target species is concentrated by several orders of magnitude as compared to the loading volume.

19. The method of claim 9, wherein the target species is concentrated by $10^6$ as compared to the loading volume.

20. The method of claim 9, wherein the target species is a protein.

21. The method of claim 20, wherein the protein is p53, islet amyloid polypeptide, beta-amyloid, tau, alpha-synuclein, huntingtin, or superoxide dismutase.

* * * * *